United States Patent
Cleve et al.

(10) Patent No.: US 7,138,421 B2
(45) Date of Patent: Nov. 21, 2006

(54) ANTI-ANDROGENIC PYRROLIDINES WITH TUMOR-INHIBITING ACTION

(75) Inventors: Arwed Cleve, Berlin (DE); Volker Schulze, Berlin (DE); Dieter Zopf, Berlin (DE); Jens Hoffmann, Muehlenbeck (DE); Andreas Reichel, Berlin (DE); Karsten Parczyk, Berlin (DE)

(73) Assignee: Schring Aktiengesellschaft, Berlin (DE)

( * ) Notice: Subject to any disclaimer, the term of this patent is extended or adjusted under 35 U.S.C. 154(b) by 47 days.

(21) Appl. No.: 10/841,825

(22) Filed: May 10, 2004

(65) Prior Publication Data

US 2005/0159468 A1 Jul. 21, 2005

Related U.S. Application Data

(60) Provisional application No. 60/470,182, filed on May 14, 2003.

(30) Foreign Application Priority Data

May 9, 2003 (DE) ................................. 103 22 108

(51) Int. Cl.
*A61K 31/4178* (2006.01)
*C07D 403/06* (2006.01)

(52) U.S. Cl. .................................... 514/391; 548/314.7
(58) Field of Classification Search ............. 548/314.7; 514/391

See application file for complete search history.

(56) References Cited

U.S. PATENT DOCUMENTS 5,411,981 A * 5/1995 Gaillard-Kelly et al. .... 514/386

FOREIGN PATENT DOCUMENTS

| WO | WO 97/00071 | 1/1997 |
|---|---|---|
| WO | WO 00/37430 | 6/2000 |

OTHER PUBLICATIONS

Golub et al., Science, vol. 286, Oct. 15, 1999, pp. 531-537.*
International Search Report dated Dec. 8, 2004 issued in PCT/EP2004/004225.
M. E. Van Dort, et al., American Chemical Society, (2000), pp. 3344-3347.

* cited by examiner

*Primary Examiner*—Laura L. Stockton
(74) *Attorney, Agent, or Firm*—Millen, White, Zelano & Branigan, P.C.

(57) ABSTRACT

This invention relates to anti-androgenic N-[ω-[3-[4-cyano-3-(trifluoromethyl)-phenyl]-5,5-dimethyl-4-oxo-2-thioxoimidazolidin-1-yl]alkyl]-substituted pyrrolidines of general formula I, with a strongly pronounced antiproliferative profile of action; process for the production of the compounds of general formula I, pharmaceutical preparations and the use for the production of pharmaceutical agents.

18 Claims, 4 Drawing Sheets

ANTI-ANDROGENIC PYRROLIDINES WITH TUMOR-INHIBITING ACTION

This application claims the benefit of the filing date of U.S. Provisional Application Ser. No. 60/470,182 filed May 14, 2003.

This invention relates to anti-androgenic N-[ω-[3-[4-cyano-3-(trifluoromethyl)-phenyl]-5,5-dimethyl-4-oxo-2-thioxoimidazolidin-1-yl]alkyl]-substituted pyrrolidines, with a strongly pronounced antiproliferative action profile, process for their production, as well as pharmaceutical preparations that contain the pyyrolidines according to the invention and their use for the production of pharmaceutical agents.

In industrialized countries, prostate cancer, after lung cancer, is the second main cause of death by cancer in men. In men over 55 years of age, 4% of all deaths can be attributed to a prostate tumor disease, and it is expected that the proportion in men over 80 increases to up to 80% of deaths. The death rate is still relatively low, but it increases yearly by about 14%. The number of men in whom a prostate tumor was diagnosed has increased by 30% in recent years, which can be attributed less to an increasing number of new diseases but rather that the population is generally older, that diagnostic processes have improved and that systematic screening programs were introduced (E. J. Small, D. M. Reese, Curr. Opi. Oncol. 2000, 12, 265–272).

The prostate tumor grows in an androgen-dependent manner in early stages. As long as the tumor is locally limited to the prostate, it can be removed by surgical intervention or by radiation therapy, whereby these methods are associated with corresponding risks. In the cases in which the tumor is no longer locally limited and has already formed metastases, the tumor is treated palliatively by reduction of the testosterone level in the blood. This is carried out either surgically by castration or medicinally by treatment with anti-androgens (bicalutamide, cyproterone acetate, flutamide), LHRH-agonists (buserelin, zoladex), LHRH-antagonists (cetrorelix) or 5α-reductase inhibitors (finasteride). Since the adrenal androgen synthesis remains unaffected in a surgical castration, more recently a combined surgical and medicinal treatment is frequently performed (S. Leewansangtong, E. D. Crawford, Endocrine-Related Cancer 1998, 5, 325–339). This treatment, however, has only temporary success, since after at the latest two years, it generally results in renewed growth of the tumor, which in most cases is then hormone-independent (L. J. Denis, K. Griffith, Semin. in Surg. Onc. 2000, 18, 52–74). Despite intensive research in the last 50 years, up until now there has been no effective treatment against these advanced stages. The 5-year survival rate in these patients is less than 15%.

There are different indications that show that the androgen receptor plays an important role in the development and the growth of the prostate tumor not only in the early hormone-dependent stages of the tumor progression, but also in late hormone-independent stages of the tumor progression.

The androgen receptor belongs to the family of steroid hormone receptors that act as transcription factors. The androgen receptor binds androgens, by which it is stabilized and protected from a quick proteolytic degradation. After hormone bonding, it is transported into the nucleus, where it activates certain genes by binding to so-called androgen-responsive DNA elements that are in promoter regions (D. J. Lamb et. al. Vitam. Horm. 2001, 62, 199–230).

Studies on prostate tumors show that in 30% of advanced tumors, an amplification of the androgen receptor gene locus was detected. In other cases, a number of mutations were found in the androgen receptor gene, which are localized in various domains of the androgen receptor molecule and result in altered receptor properties. Mutated receptors can either have a higher affinity for androgens, be constitutively active, change their ligand specificity, so that they are activated by other steroid hormones or even anti-androgens, be activated via interactions with molecules from other growth-promoting signal-transmitting methods, change the interaction with cofactors, or activate other target genes (J. P. Elo, T. Visakorpi, Ann. Med. 2001, 33, 130–41).

The identification of anti-androgens, which inhibit not only the natural androgen receptor but also its mutated forms and have an enhanced antiproliferative effect on tumor cells, would presumably be very helpful in treating prostate tumors in various stages. Such compounds can significantly change the period until the tumor growth recurs.

Studies with nonsteroidal anti-androgens have shown that they have advantages compared to the steroidal compounds and are therefore to be preferred. Thus, with nonsteroidal compounds, a more selective action with fewer adverse side effects can be achieved. In contrast to the steroidal anti-androgens, the known nonsteroids bicalutamide and flutamide lack, e.g., the progestagenic activity, and in addition, their use results in an increase in the testosterone level in the serum, which clinically could result in development of potency (P. Reid, P. Kantoff, W. Oh, Investigational New Drugs 1999, 17, 271–284).

Nonsteroidal anti-androgens are described in U.S. Pat. No. 5,411,981 or U.S. Pat. No. Re. 35,956 (phenylimidazolidine derivatives), in WO 97/00071 (specifically substituted phenyldimethyl hydantoins as well as their imino- or thione derivatives), in WO 00/37430 (phenylalanine, phenyl hydantoins as well as phenyl ureas), in WO 01/58855 (aminopropanilides) and in EP 1122242 (substituted U.S. Pat. No. Re. 35,956 cyanophenylpiperazine describes, i.a., [4-cyano-3-(trifluoromethyl)phenyl]-substituted thiohydantoins with a short-chain, terminally substituted radical, whereby in the case of the chain, this is preferably a $C_1$–$C_4$-chain.

The compounds that are explicitly disclosed in U.S. Pat. No. Re. 35,956 have an anti-androgenic action, but only a slightly antiproliferative action in cells that originate from human prostate cancers.

For an effective therapy of androgen-dependent tumors and/or other proliferative diseases, an additional antiproliferative action is necessary.

The object of this invention therefore consists in making available orally bioavailable anti-androgenic compounds with increased antiproliferative action that can inhibit the growth of androgen-dependent benign or malignant tumors or alleviate or heal androgen-dependent proliferative diseases.

This object is achieved according to the invention by the N-[ω-[3-[4-cyano-3-(trifluoromethyl)phenyl]-5,5-dimethyl-4-oxo-2-thioxoimidazolidin-1-yl]alkyl]-substituted pyrrolidines of general formula I:

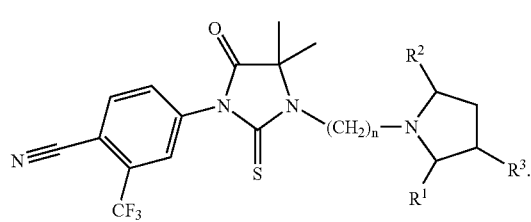

in which n can mean an integer between 6 and 9, $R^1$ and $R^2$, independently of one another, can mean a hydrogen atom, an unbranched $C_1$–$C_4$-alkyl group, a branched $C_3$–$C_5$-alkyl group, an unbranched hydroxy-$C_1$–$C_4$-alkyl group, a branched hydroxy-$C_3$–$CS_5$-alkyl group, an unbranched $C_1$–$C_4$-alkoxy-$C_1$–$C_4$-alkyl group, a branched $C_1$–$C_4$-alkoxy-$C_3$–$C_5$-alkyl group, an unbranched $C_1$–$C_4$-alkanoyloxy-$C_1$–$C_4$-alkyl group, a branched $C_1$–$C_4$-alkanoyloxy-$C_3$–$C_5$-alkyl group, a (pyrrolidin-1-yl)methyl group, a carboxy group, a $C_1$–$C_4$-alkoxycarbonyl group or an aminocarbonyl group, or $R^1$ and $R^2$ together can mean a 2-hydroxypropane-1,3-diyl bridge;

$R^3$ can mean a hydrogen atom or a hydroxy group.

It was found that the antiproliferative action of compounds of the N-[3-[4-cyano-3-(trifluoromethyl)phenyl]-5,5-dimethylthiohydantoin type can be increased, surprisingly enough, while retaining anti-androgenic activity, if the N-1-nitrogen carries a pyrrolidin-1-ylalkyl substituent. The compounds according to the invention are distinguished by an alkylene chain of a defined length range, which connects the pyrrolidine nucleus to the thiohydantoin nucleus. Depending on the combination of the heterocyclic end group with the length of the alkylene chain that connects the latter with the thiohydantoin nucleus, a more or less pronounced additional effect that results in the destabilization of the androgen receptor can occur.

This invention comprises a process for the production of the compounds of general formula I according to the invention, in which compounds of general formula II

II in which n can mean an integer between 6 and 9,

X can mean a leaving group, are reacted in the presence of an organic base with compounds of general formula III

III in which $R^1$ and $R^2$, independently of one another, can mean a hydrogen atom, an unbranched $C_1$–$C_4$-alkyl group, a branched $C_3$–$C_5$-alkyl group, an unbranched hydroxy-$C_1$–$C_4$-alkyl group, a branched hydroxy-$C_3$–$C_5$-alkyl group, an unbranched $C_1$–$C_4$-alkoxy-$C_1$–$C_4$-alkyl group, a branched $C_1$–$C_4$-alkoxy-$C_3$–$C_5$-alkyl group, an unbranched $C_1$–$C_4$-alkanoyloxy -$C_1$–$C_4$-alkyl group, a branched $C_1$–$C_4$-alkanoyloxy-$C_3$–$C_5$-alkyl group, a (pyrrolidin-1-yl)methyl group, a carboxy group, a $C_1$–$C_4$-alkoxycarbonyl group or an aminocarbonyl group, or $R^1$ and $R^2$ together can mean a 2-hydroxypropane-1,3-diyl bridge;

$R^3$ can mean a hydrogen atom or a hydroxy group.

Alkenyl chain —$CH_2$)$_n$— is the n-hexylene, n-heptylene, n-octylene or n-nonylene group.

The unbranched hydroxy-$C_1$–$C_4$-alkyl group can be a hydroxymethyl-($HOCH_2$—), 2-hydroxyethyl-($HOCH_2CH_2$—), 1-hydroxyethyl-[$CH_3CH(OH)$—], 3-hydroxypropyl -($HOCH_2CH_2CH_2$—), 2-hydroxypropyl-[$CH_3CH(OH)CH_2CH_2$—], 1-hydroxypropyl-[$CH_3CH_2CH(OH)$—], 4-hydroxybutyl-($HOCH_2CH_2CH_2CH_2$—), 3-hydroxybutyl-[$CH_3CH(OH)CH_2CH_2$—], 2-hydroxybutyl-[$CH_3CH_2CH(OH)CH_2$—] or 1-hydroxybutyl [$CH_3CH_2CH_2CH(OH)$] group.

The branched hydroxy-$C_3$–$C_5$-alkyl group can be a 1-hydroxy-1-methylethyl-[$(CH_3)_2C(OH)$—], 2-hydroxy-1-methylethyl-[$HOCH_2CH(CH_3)$—], 1-hydroxy-1-methylpropyl-[$CH_3CH_2C(CH_3)(OH)$—], 2-hydroxy-1-methylpropyl-[$CH_3CH(OH)CH(CH_3)$—], 3-hydroxy-1-methylpropyl-[$HOCH_2CH_2CH(CH_3)$—], 1-(hydroxymethyl)propyl-[$CH_3CH_2C(CH_2OH)$—], 1-hydroxy-2-methylpropyl-[$(CH_3)_2CHCH(OH)$—], 2-hydroxy-2-methylpropyl-[$CH_3C(OH)(CH_3)CH_2$—], 3-hydroxy-2-methylpropyl-[$HOCH_2CH(CH_3)CH_2$—], 1-(hydroxymethyl)butyl-[$CH_3CH_2CH_2CH(CH_2OH)$—], 1-hydroxy-1-methylbutyl-[$CH_3CH_2CH_2C(CH_3)$ $(OH)$—], 2-hydroxy-1-methylbutyl-[$CH_3CH_2CH(OH)CH(CH_3)$—], 3-hydroxy-1-methylbutyl-[$CH_3CH(OH)CH_2CH(CH_3)$—], 4-hydroxy-1-methylbutyl-[$HOCH_2CH_2CH_2CH(CH_3)$—], 3-hydroxy-1-ethylpropyl-[$HOCH_2CH_2CH(CH_2CH_3)$—], 2-hydroxy-1-ethylpropyl-[$CH_3CH(OH)CH(CH_2CH_3)$—], 1-hydroxy-1-ethylpropyl-[$CH_3CH_2C(CH_2CH_3)(OH)$—], 1-hydroxy-3-methylbutyl-[$CH_3CH(CH_3)CH_2CH(OH)$—], 2-hydroxy-3-methylbutyl-[$(CH_3)_2CHCH(OH)CH_2$—], 3-hydroxy-3-methylbutyl-[$CH_3C(CH_3)(OH)CH_2CH_2$—], 4-hydroxy-3-methylbutyl-[$HOCH_2CH(CH_3)CH_2CH_2$—], 1-(hydroxymethyl)-1-methylpropyl-[$CH_3CH_2C(CH_3)(CH_2OH)$—], 2-hydroxy-1,1-dimethylpropyl-[$CH_3CH(OH)C(CH_{32}$—], 3-hydroxy-1,1-dimethylpropyl-[$HOCH_2CH_2C(CH_3)_2$—], 1-(hydroxymethyl)-2-methylpropyl-[$(CH_3)_2CHCH$ $(CH_2OH)$—], 1-hydroxy-1,2-dimethylpropyl-[$(CH_3)_2CHC(OH)(CH_3)$—], 2-hydroxy-1,2-dimethylpropyl-[$(CH_3)_2C(OH)CH(CH_3)$—], 3-hydroxy-1,2-dimethylpropyl-[$HOCH_2CH(CH_3)CH(CH_3)$—], 1-hydroxy-2,2-dimethylpropyl-[$(CH_3)_3CCH(OH)$—], 3-hydroxy-2,2-dimethylpropyl-[$HOCH_2C(CH_3)_2CH_2$—], 1-hydroxy-2-methylbutyl-[$CH_3CH_2CH(CH_3)CH(OH)$—], 2-hydroxy-2-methylbutyl-[$CH_3CH_2C(CH_3)(OH)CH_2$—], 3-hydroxy-2-methylbutyl-[$CH_3CH(OH)CH(CH_3)CH_2$—], 4-hydroxy-2-methylbutyl-[$HOCH_2CH_2CH(CH_3)CH_2$—] or 3-hydroxy-2-ethylpropyl-[$HOCH_2CH(CH_2CH_3)CH_2$—] group.

The unbranched $C_1$–$C_4$-alkoxy-$C_1$–$C_4$-alkylene group can be an alkoxymethyl-($AlkOCH_2$—), 2-alkoxyethyl-($AlkOCH_2CH_2$—), 1-alkoxyethyl-[$CH_3CH(OAlk)$—], 3-alkoxypropyl-($AlkOCH_2CH_2CH_2$—), 2-alkoxypropyl-[$CH_3CH(OAlk)CH_2CH_2$—], 1-alkoxypropyl-[$CH_3CH_2CH(OAlk)$—], 4-alkoxybutyl-($AlkOCH_2CH_2CH_2CH_2$—), 3-alkoxybutyl-[$CH_3CH(OAlk)CH_2CH_2$—], 2-alkoxybutyl-[$CH_3CH_2CH(OAlk)CH_2$—] or 1-alkoxybutyl [$CH_3CH_2CH_2CH(OAlk)$—] group.

The branched $C_1$–$C_4$-alkoxy-$C_3$–$C_5$-alkyl group can be a 1-alkoxy-1-methylethyl-[$(CH_3)_2C(OAlk)$—], 2-alkoxy-1-methylethyl-[$AlkOCH_2CH(CH_3)$—], 1-alkoxy-1-methylpropyl-[CH$_3$CH$_2$C(CH$_3$)(OAlk)—], 2-alkoxy-1-methylpropyl-[CH$_3$CH(OAlk)CH(CH$_3$)—], 3-alkoxy-1-methylpropyl-[AlkOCH$_2$CH$_2$CH(CH$_3$)—], 1-(alkoxymethyl)propyl-[CH$_3$CH$_2$C(CH$_2$OAlk)—], 1-alkoxy-2-methylpropyl-[(CH$_3$)$_2$CHCH(OAlk)—], 2-alkoxy-2-methylpropyl-[CH$_3$C(OAlk)(CH$_3$)CH$_2$—], 3-alkoxy-2-methylpropyl-[AlkOCH$_2$CH(CH$_3$)CH$_2$—], 1-(alkoxymethyl)butyl-[CH$_3$CH$_2$CH$_2$CH(CH$_2$OAlk)—], 1-alkoxy-1-methylbutyl-[CH$_3$CH$_2$CH$_2$C(CH$_3$) (OAlk)—], 2-alkoxy-1-methylbutyl-[CH$_3$CH$_2$CH(OAlk)CH(CH$_3$)—], 3-alkoxy-1-methylbutyl-[CH$_3$CH(OAlk)CH$_2$CH(CH$_3$)—], 4-alkoxy-1-methylbutyl-[AlkOCH$_2$CH$_2$CH$_2$CH(CH$_3$)—], 3-alkoxy-1-ethylpropyl-[AlkOCH$_2$CH$_2$CH(CH$_2$CH$_3$)—], 2-alkoxy-1-ethylpropyl-[CH$_3$CH(OAlk)CH(CH$_2$CH$_3$)—], 1-alkoxy-1-ethylpropyl-[CH$_3$CH$_2$C(CH$_2$CH$_3$)(OAlk)—], 1-alkoxy-3-methylbutyl-[CH$_3$CH(CH$_3$)CH$_2$CH(OAlk)—], 2-alkoxy-3-methylbutyl-[(CH$_3$)$_2$CHCH(OAlk)CH$_2$—], 3-alkoxy-3-methylbutyl-[CH$_3$C(CH$_3$)(OAlk)CH$_2$CH$_2$—], 4-alkoxy-3-methylbutyl-[AlkOCH$_2$CH(CH$_3$)CH$_2$CH$_2$—], 1-(alkoxymethyl)-1-methylpropyl-[CH$_3$CH$_2$C(CH$_3$)(CH$_2$OAlk)—], 2-alkoxy-1,1-dimethylpropyl-[CH$_3$CH(OAlk)C(CH$_3$)$_2$—], 3-alkoxy-1,1-dimethylpropyl-[AlkOCH$_2$CH$_2$C(CH$_3$)$_2$—], 1-(alkoxymethyl)-2-methylpropyl-[(CH$_3$)$_2$CHCH(CH$_2$OAlk)—], 1-alkoxy-1,2-dimethylpropyl-[(CH$_3$)$_2$CHC(OAlk)(CH$_3$)—], 2-alkoxy-1,2-dimethylpropyl-[(CH$_3$)$_2$C(OAlk)CH(CH$_3$)—], 3-alkoxy-1,2-dimethylpropyl-[AlkOCH$_2$CH(CH$_3$)—CH(CH$_3$)—], 1-alkoxy-2,2-dimethylpropyl-[(CH$_3$)$_3$CCH(OAlk)—], 3-alkoxy-2,2-dimethylpropyl-[AlkOCH$_2$C(CH$_3$)$_2$CH$_2$—], 1-alkoxy-2-methylbutyl-[CH$_3$CH$_2$CH(CH$_3$)CH(OAlk)—], 2-alkoxy-2-methylbutyl-[CH$_3$CH$_2$C(CH$_3$)(OAlk)CH$_2$—], 3-alkoxy-2-methylbutyl-[CH$_3$CH(OAlk)CH(CH$_3$)CH$_2$—], 4-alkoxy-2-methylbutyl-[AlkOCH$_2$CH$_2$CH(CH$_3$)CH$_2$—] or 3-alkoxy-2-ethylpropyl-[AlkOCH$_2$CH(CH$_2$CH$_3$)CH$_2$—] group.

The $C_1$–$C_4$-alkoxy group can be, for example, a methoxy-, ethoxy-, n-propoxy-, iso-propoxy-, n-butoxy-, sec-butoxy-, iso-butoxy- or tert-butoxy group.

The $C_1$–$C_4$-alkanoyl group can be, for example, a formyl-, acetyl-, propanoyl-, butanoyl- or iso-butanoyl group.

The unbranched $C_1$–$C_4$-alkanoyloxy-$C_1$–$C_4$-alkylene group can be an alkanoyloxymethyl-(AlkCOOCH$_2$—), 2-alkanoyloxyethyl-(AlkCOOCH$_2$CH$_2$—), 1-alkanoyloxyethyl-[CH$_3$CH(OCOAlk)—], 3-alkanoyloxypropyl-(AlkCOOCH$_2$CH$_2$CH$_2$—), 2-alkanoyloxypropyl-[CH$_3$CH(OCOAlk)CH$_2$CH$_2$—], 1-alkanoyloxypropyl-[CH$_3$CH$_2$CH(OCOAlk)—], 4-alkanoyloxybutyl-(AlkCOOCH$_2$CH$_2$CH$_2$CH$_2$—), 3-alkanoyloxybutyl-[CH$_3$CH(OCOAlk)CH$_2$CH$_2$—], 2-alkanoyloxybutyl-[CH$_3$CH$_2$CH(OCOAlk)CH$_2$—] or 1-alkanoyloxybutyl [CH$_3$CH$_2$CH$_2$CH(OCOAlk)—] group.

The branched $C_1$–$C_4$-alkanoyloxy-$C_3$–$C_5$-alkyl group can be a 1-alkanoyloxy-1-methylethyl-[(CH$_3$)$_2$C(OCOAlk)—], 2-alkanoyloxy-1-methylethyl-[Alk-COOCH$_2$CH(CH$_3$)—], 1-alkanoyloxy-1-methylpropyl-[CH$_3$CH$_2$C(CH$_3$)(OCOAlk)—], 2-alkanoyloxy-1-methylpropyl-[CH$_3$CH(OCOAlk)CH(CH$_3$)—], 3-alkanoyloxy-1-methylpropyl-[AlkCOOCH$_2$CH$_2$CH(CH$_3$)—], 1-(alkanoyloxymethyl)propyl-[CH$_3$CH$_2$C(CH$_2$OCOAlk)—], 1-alkanoyloxy-2-methylpropyl-[(CH$_3$)$_2$CHCH(OCOAlk)—], 2-alkanoyloxy-2-methylpropyl-[CH$_3$C(OCOAlk)(CH$_3$)CH$_2$—], 3-alkanoyloxy-2-methylpropyl-[AlkCOOCH$_2$CH(CH$_3$)CH$_2$—], 1-(alkanoyloxymethyl)butyl-[CH$_3$CH$_2$CH$_2$CH(CH$_2$OCOAlk)—], 1-alkanoyloxy-1-methylbutyl-[CH$_3$CH$_2$CH$_2$C(CH$_3$)(OCOAlk)—], 2-alkanoyloxy-1-methylbutyl-[CH$_3$CH$_2$CH(OCOAlk)CH(CH$_3$)—], 3-alkanoyloxy-1-methylbutyl-[CH$_3$CH(OCOAlk)CH$_2$CH(CH$_3$)—], 4-alkanoyloxy-1-methylbutyl-[AlkCOOCH$_2$CH$_2$CH$_2$CH(CH$_3$)—], 3-alkanoyloxy-1-ethylpropyl-[Alk-COOCH$_2$CH$_2$CH(CH$_2$CH$_3$)—], 2-alkanoyloxy-1-ethylpropyl-[CH$_3$CH(OCOAlk)CH(CH$_2$CH$_3$)—], 1-alkanoyloxy-1-ethylpropyl-[CH$_3$CH$_2$C(CH$_2$CH$_3$)(OCOAlk)—], 1-alkanoyloxy-3-methylbutyl-[CH$_3$CH(CH$_3$)CH$_2$CH(OCOAlk)—], 2-alkanoyloxy-3-methylbutyl-[(CH$_3$)$_2$CHCH(OCOAlk)CH$_2$—], 3-alkanoyloxy-3-methylbutyl-[CH$_3$C(CH$_3$)(OCOAlk)CH$_2$CH$_2$—], 4-alkanoyloxy-3-methylbutyl-[Alk-COOCH$_2$CH(CH$_3$)CH$_2$CH$_2$—], 1-(alkanoyloxymethyl)-1-methylpropyl-[CH$_3$CH$_2$C(CH$_3$)(CH$_2$OCOAlk)—], 2-alkanoyloxy-1,1-dimethylpropyl-[CH$_3$CH(OCOAlk)C(CH$_{32}$—], 3-alkanoyloxy-1,1-dimethylpropyl-[Alk-COOCH$_2$CH$_2$C(CH$_{32}$—], 1-(alkanoyloxymethyl)-2-methylpropyl-[(CH$_3$)$_2$CHCH(CH$_2$OCOAlk)—], 1-alkanoyloxy-1,2-dimethylpropyl-[(CH$_3$)$_2$CHC(OCOAlk)(CH$_3$)—], 2-alkanoyloxy-1,2-dimethylpropyl-[(CH$_3$)$_2$C(OCOAlk)CH(CH$_3$)—], 3-alkanoyloxy-1,2-dimethylpropyl-[Alk-COOCH$_2$CH(CH$_3$)CH(CH$_3$)—], 1-alkanoyloxy-2,2-dimethylpropyl-[(CH$_3$)$_3$CCH(OCOAlk)—], 3-alkanoyloxy-2,2-dimethylpropyl-[Alk-COOCH$_2$C(CH$_3$)$_2$CH$_2$—], 1-alkanoyloxy-2-methylbutyl-[CH$_3$CH$_2$CH(CH$_3$)CH(OCOAlk)—], 2-alkanoyloxy-2-methylbutyl-[CH$_3$CH$_2$C(CH$_3$)(OCOAlk)CH$_2$—], 3-alkanoyloxy-2-methylbutyl-[CH$_3$CH(OCOAlk)CH(CH$_3$)CH$_2$—], 4-alkanoyloxy-2-methylbutyl-[Alk-COOCH$_2$CH$_2$CH(CH$_3$)CH$_2$—] or 3-alkanoyloxy-2-ethylpropyl [Alk-COOCH$_2$CH(CH$_2$CH$_3$)CH$_2$—] group.

Leaving group X can be a halogen or a sulfonic ester group.

Halogen can be chlorine, bromine or iodine, whereby iodine is preferred.

The sulfonic ester group can be, for example, a mesylate, benzenesulfonate, tosylate, brosylate, triflate or nonaflate group.

The organic base is a tertiary amine or amide base, such as, for example, triethylamine or ethyl diisopropylamine.

For the formation of pharmaceutically compatible salts of the compounds of general formula I according to the invention, according to the methods that are known to one skilled in the art, i.a., hydrochloric acid, hydrobromic acid, sulfuric acid and phosphoric acid and nitric acid can be considered as inorganic acids; i.a., acetic acid, propionic acid, hexanoic acid, octanoic acid, decanoic acid, oleic acid, stearic acid, maleic acid, fumaric acid, succinic acid, benzoic acid, ascorbic acid, oxalic acid, salicylic acid, tartaric acid, citric acid, lactic acid, glycolic acid, malic acid, mandelic acid, cinnamic acid, glutaminic acid, and asparaginic acid can be considered as carboxylic acids; and i.a., methanesulfonic acid, ethanesulfonic acid, toluenesulfonic acid, benzenesulfonic acid as well as naphthalenesulfonic acid can be considered as sulfonic acids.

Examples 1 to 58 of the compounds according to the invention that are mentioned below under the Chapter "Production Process" are especially preferred.

Pharmacological Studies

The compounds according to the invention were tested in various models. The compounds of general formula I according to the invention are distinguished in that in this case, these are compounds with anti-androgenic action that inhibit prostate tumor growth, simultaneously have a high, optionally oral bioavailability and optionally destabilize the androgen receptor.

The in vitro tests on the influences on the activities of the androgen receptor were performed as follows:

The following abbreviations are used:
Bicalutamide: N-[4-Cyano-3-(trifluoromethyl)phenyl]-3-[(4-fluorophenyl)sulfonyl]-2-hydroxy-2-methylpropanamide
R1881: Methyltrienolone, 17β-hydroxy-17α-methyl-estra-4,9,11-trien-3-one
CPA: Cyproterone acetate, 17-(acetyloxy)-6-chloro-1β,2β-dihydro-3'H-cyclopropa[1,2]pregna-1,4,6-triene-3,20-dione Model 1: Inhibition of the Proliferation of LNCaP Cells For the proliferation assay, 6000 LNCaP cells/well (Horoszewicz et al. Cancer Res. 1983, 43, 1809–1817) in a microtiter plate (96-well) in 50 µl of RPMI1640 medium are grown with 5% CCS and cultivated as in Model 1. After 24 hours, the cells receive 50 µl of 2×-concentrated test substance, diluted in culture medium. The solvent concentration is 0.5% DMSO. After 4 days, the cells receive another 100 µl of 1×-concentrated test substance, diluted in culture medium. After 7 to 8 days, the proliferation rate of the cells is determined by means of crystal violet assay (Gillies et al. Anal. Biochem. 1986, 159, 109–113). To determine the antagonism, the substance treatment is performed in the presence of 0.1 nmol of R1881 (1:1000 dilution of ethanolic solution). Control cells receive only 0.5% DMSO. For the agonism, the cells are treated only with test substance (without R1881).

Table 1 shows the inhibitory action of test substances on the proliferation of the human androgen-dependent prostate cell line LNCaP. The inhibition of the cell proliferation is an important requirement for the therapeutic use of the substances in the treatment of prostate cancer. The selected test substances according to the invention inhibit the cell proliferation in the presence of 0.1 nmol of the synthetic androgen R1881 with a considerably lower $IC_{50}$ (about $50 \times 10^{-9}$ M), such as the approved nonsteroidal anti-androgen bicalutamide ($380 \times 10^{-9}$ M). At a substance concentration of 1 µmol, the proliferation compared to the cell growth in the presence of 0.1 nmol of R1881 is reduced by at least 80%. Up to a tested concentration of 10 µmol, a proliferation-stimulating action was observed in none of the test substances It has been found, surprisingly enough, that the extent of the proliferation-inhibiting action of N-[ω-[3-[4-cyano-3-(trifluoromethyl)phenyl]-5,5-dimethyl-4-oxo-2-thioxoimidazolidin-1-yl]alkyl] derivatives is simultaneously dependent on chain substituents and the chain length. Especially for the pyrrolidine-substituted compounds that are claimed here, the strongest antiproliferative action is observed in chain lengths between $C_6$ and $C_9$. Analogous compounds with shorter chain lengths n=4 (comparison 1) and n=5 (comparison 2) show a considerably reduced antiproliferative activity. For the tested examples from U.S. Pat. No. Re. 35,956 [Examples 71 and 77] of the chain length n=2 and 4, little or no antiproliferative action could be detected.

TABLE 1

| Example | Test Substance | IC50 [$10^{-9}$ M] | % Inhibition at 1 µM |
|---|---|---|---|
| Inhibition of the Proliferation of LNCaP Cells by Test Substances. | | | |
| Bicalutamide | N-[4-Cyano-3-(trifluoromethyl)phenyl]-3-[(4-fluorophenyl)sulfonyl]-2-hydroxy-2-methylpropanamide | 380 | 85 |
| Comparison 1 | 4-[4,4-Dimethyl-5-oxo-3-[4-(pyrrolidin-1-yl)butyl]-2-thioxoimidazolidin-1-yl]-2-(trifluoromethyl)benzonitrile | 4300 | 20 |
| Comparison 2 | 4-[4,4-Dimethyl-5-oxo-3-[5-(pyrrolidin-1-yl)pentyl]-2-thioxoimidazolidin-1-yl]-2-(trifluoromethyl)benzonitrile | 2100 | 38 |
| Example 71 USRe 35956 | 4-[3-(2-Hydroxyethyl)-4,4-dimethyl-5-oxo-2-thioxoimidazolidin-1-yl]-2-(trifluoromethyl)benzonitrile | >10000 | 9 |
| Example 77 USRe 35956 | 4-[3-(4-Hydroxybutyl)-4,4-dimethyl-5-oxo-2-thioxoimidazolidin-1-yl]-2-(trifluoromethyl)benzonitrile | >10000 | 34 |
| 1 | 4-[4,4-Dimethyl-5-oxo-3-[8-(pyrrolidin-1-yl)octyl]-2-thioxoimidazolidin-1-yl]-2-(trifluoromethyl)benzonitrile | 45 | 98 |
| 2 | 4-[4,4-Dimethyl-5-oxo-3-[8-(pyrrolidin-1-yl)octyl]-2-thioxoimidazolidin-1-yl]-2-(trifluoromethyl)benzonitrile hydrochloride | 41 | 100 |
| 4 | 4-[4,4-Dimethyl-5-oxo-3-[7-(pyrrolidin-1-yl)heptyl]-2-thioxoimidazolidin-1-yl]-2-(trifluoromethyl)benzonitrile | 45 | 98 |
| 6 | 4-[3-[6-[(2R)-2-(Hydroxymethyl)pyrrolidin-1-yl]hexyl]-4,4-dimethyl-5-oxo-2-thioxoimidazolidin-1-yl]-2-(trifluoromethyl)benzonitrile | 55 | 102 |
| 8 | 4-[3-[7-[(2R)-2-(Hydroxymethyl)pyrrolidin-1-yl]heptyl]-4,4-dimethyl-5-oxo-2-thioxoimidazolidin-1-yl]-2-(trifluoromethyl)benzonitrile | 11 | 101 |
| 9 | 4-[3-[7-[(2S)-2-(Hydroxymethyl)pyrrolidin-1-yl]heptyl]-4,4-dimethyl-5-oxo-2-thioxoimidazolidin-1-yl]-2-(trifluoromethyl)benzonitrile | 26 | 92 |

TABLE 1-continued

| Example | Test Substance | IC50 [$10^{-9}$ M] | % Inhibition at 1 μM |
|---|---|---|---|
| 10 | 4-[3-[8-[(2R)-2-(Hydroxymethyl)pyrrolidin-1-yl]octyl]-4,4-dimethyl-5-oxo-2-thioxoimidazolidin-1-yl]-2-(trifluoromethyl)benzonitrile | <10 | 101 |
| 11 | 4-[3-[8-[(2S)-2-(Hydroxymethyl)pyrrolidin-1-yl]octyl]-4,4-dimethyl-5-oxo-2-thioxoimidazolidin-1-yl]-2-(trifluoromethyl)benzonitrile | 13 | 102 |
| 12 | 4-[3-[9-[(2R)-2-(Hydroxymethyl)pyrrolidin-1-yl]nonyl]-4,4-dimethyl-5-oxo-2-thioxoimidazolidin-1-yl]-2-(trifluoromethyl)benzonitrile | 24 | 93 |
| 13 | 4-[3-[9-[(2S)-2-(Hydroxymethyl)pyrrolidin-1-yl]nonyl]-4,4-dimethyl-5-oxo-2-thioxoimidazolidin-1-yl]-2-(trifluoromethyl)benzonitrile | 16 | 88 |
| 16 | 4-[3-[7-[(2R)-2-(Methoxymethyl)pyrrolidin-1-yl]heptyl]-4,4-dimethyl-5-oxo-2-thioxoimidazolidin-1-yl]-2-(trifluoromethyl)benzonitrile | 18 | 98 |
| 17 | 4-[3-[7-[(2S)-2-(Methoxymethyl)pyrrolidin-1-yl]heptyl]-4,4-dimethyl-5-oxo-2-thioxoimidazolidin-1-yl]-2-(trifluoromethyl)benzonitrile | 32 | 99 |
| 18 | 4-[3-[8-[(2R)-2-(Methoxymethyl)pyrrolidin-1-yl]octyl]-4,4-dimethyl-5-oxo-2-thioxoimidazolidin-1-yl]-2-(trifluoromethyl)benzonitrile | 11 | 103 |
| 19 | 4-[3-[8-[(2S)-2-(Methoxymethyl)pyrrolidin-1-yl]octyl]-4,4-dimethyl-5-oxo-2-thioxoimidazolidin-1-yl]-2-(trifluoromethyl)benzonitrile | 25 | 97 |
| 20 | 4-[3-[9-[(2R)-2-(Methoxymethyl)pyrrolidin-1-yl]nonyl]-4,4-dimethyl-5-oxo-2-thioxoimidazolidin-1-yl]-2-(trifluoromethyl)benzonitrile | 29 | 101 |
| 21 | 4-[3-[9-[(2S)-2-(Methoxymethyl)pyrrolidin-1-yl]nonyl]-4,4-dimethyl-5-oxo-2-thioxoimidazolidin-1-yl]-2-(trifluoromethyl)benzonitrile | 47 | 94 |
| 23 | 4-[3-[7-(3-Hydroxy-8-azabicyclo[3.2.1]oct-8-yl)heptyl]-4,4-dimethyl-5-oxo-2-thioxoimidazolidin-1-yl]-2-(trifluoromethyl)benzonitrile | 48 | 79 |
| 24 | 4-[3-[8-(3-Hydroxy-8-azabicyclo[3.2.1]oct-8-yl)octyl]-4,4-dimethyl-5-oxo-2-thioxoimidazolidin-1-yl]-2-(trifluoromethyl)benzonitrile | 13 | 102 |
| Inhibition of the Proliferation of LNCaP Cells through Test Substances. | | | |
| 27 | 4-[3-[7-[(R)-3-Hydroxypyrrolidin-1-yl]heptyl]-4,4-dimethyl-5-oxo-2-thioxoimidazolidin-1-yl]-2-(trifluoromethyl)benzonitrile | 57 | 95 |
| 28 | 4-[3-[8-[(R)-3-Hydroxypyrrolidin-1-yl]octyl]-4,4-dimethyl-5-oxo-2-thioxoimidazolidin-1-yl]-2-(trifluoromethyl)benzonitrile | 11 | 102 |
| 29 | 4-[3-[9-[(R)-3-Hydroxypyrrolidin-1-yl]nonyl]-4,4-dimethyl-5-oxo-2-thioxoimidazolidin-1-yl]-2-(trifluoromethyl)benzonitrile | 35 | 99 |
| 31 | 4-[3-[7-[(S)-3-Hydroxypyrrolidin-1-yl]heptyl]-4,4-dimethyl-5-oxo-2-thioxoimidazolidin-1-yl]-2-(trifluoromethyl)benzonitrile | 20 | 104 |
| 32 | 4-[3-[8-[(S)-3-Hydroxypyrrolidin-1-yl]octyl]-4,4-dimethyl-5-oxo-2-thioxoimidazolidin-1-yl]-2-(trifluoromethyl)benzonitrile | 12 | 101 |
| 35 | 4-[4,4-Dimethyl-3-[7-(2-methylpyrrolidin-1-yl)heptyl]-5-oxo-2-thioxoimidazolidin-1-yl]-2-(trifluoromethyl)benzonitrile | 30 | 92 |
| 36 | 4-[4,4-Dimethyl-3-[8-(2-methylpyrrolidin-1-yl)octyl]-5-oxo-2-thioxoimidazolidin-1-yl]-2-(trifluoromethyl)benzonitrile | 15 | 96 |
| 37 | 4-[3-[8-[(2R,5S)-rel-2,5-Dimethylpyrrolidin-1-yl]octyl]-4,4-dimethyl-5-oxo-2-thioxoimidazolidin-1-yl]-2-(trifluoromethyl)benzonitrile | 11 | 99 |
| 39 | 4-[3-[7-[(2S)-2-(1-Hydroxy-1-methylethyl)pyrrolidin-1-yl]heptyl]-4,4-dimethyl-5-oxo-2-thioxoimidazolidin-1-yl]-2-(trifluoromethyl)benzonitrile | 41 | 108 |
| 40 | 4-[3-[8-[(2S)-2-(1-Hydroxy-1-methylethyl)pyrrolidin-1-yl]octyl]-4,4-dimethyl-5-oxo-2-thioxoimidazolidin-1-yl]-2-(trifluoromethyl)benzonitrile | 11 | 118 |

TABLE 1-continued

| Example | Test Substance | IC50 [10$^{-9}$ M] | % Inhibition at 1 μM |
|---|---|---|---|
| 41 | 4-[3-[9-[(2S)-2-(1-Hydroxy-1-methylethyl)pyrrolidin-1-yl]nonyl]-4,4-dimethyl-5-oxo-2-thioxoimidazolidin-1-yl]-2-(trifluoromethyl)benzonitrile | 48 | 89 |
| | Inhibition of the Proliferation of LNCaP Cells by Test Substances. | | |
| 43 | 4-[3-[7-[(2R)-2-(1-Hydroxy-1-methylethyl)pyrrolidin-1-yl]heptyl]-4,4-dimethyl-5-oxo-2-thioxoimidazolidin-1-yl]-2-(trifluoromethyl)benzonitrile | 26 | 113 |
| 44 | 4-[3-[8-[(2R)-2-(1-Hydroxy-1-methylethyl)pyrrolidin-1-yl]octyl]-4,4-dimethyl-5-oxo-2-thioxoimidazolidin-1-yl]-2-(trifluoromethyl)benzonitrile | 11 | 115 |
| 47 | 4-[3-[8-[(2S)-2-(1-Hydroxy-1-ethylpropyl)pyrrolidin-1-yl]octyl]-4,4-dimethyl-5-oxo-2-thioxoimidazolidin-1-yl]-2-(trifluoromethyl)benzonitrile | 27 | 99 |
| 49 | (S)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide | 32 | 110 |
| 50 | (S)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide | 15 | 110 |
| 51 | (S)-1-[8-[3-[4-Cyano-3-(trifluoromethyl)phenyl]-5,5-dimethyl-4-oxo-2-thioxoimidazolidin-1-yl]octyl]pyrrolidine-4-carboxamide | 20 | 97 |
| 52 | (R)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide | 12 | 100 |
| 53 | (R)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide | 49 | 97 |
| 54 | (R)-1-[8-[3-[4-Cyano-3-(trifluoromethyl)phenyl]-5,5-dimethyl-4-oxo-2-thioxoimidazolidin-1-yl]octyl]pyrrolidine-4-carboxamide | 64 | 93 |

Model 2: Anti-Androgenic Action of Selective Test Substances on the Growth of the Accessory Reproductive Glands of Mice The function and the size of accessory reproductive glands (prostate and seminal vesicles) depend on androgens. In castrated animals, a growth of these organs is induced by the administration of androgen. Simultaneous treatment with anti-androgens inhibits this growth in a dose-dependent manner.

For the examination of test substances, the mice were castrated. On the same day, treatment with testosterone propionate (0.03 mg/mouse) and the test substances (1× daily 10 or 30 mg/kg p.o. in benzyl benzoate-castor oil or ethanol/peanut oil (10:90)) was formulated. The treatment was carried out over 7 days and at the end of the test, the weights of the seminal vesicles and prostate were determined. The inhibition of the seminal vesicle growth, in percent, was calculated in reference to the control groups (with and without testosterone). As a reference substance, cyproterone acetate (30 mg/kg s.c. and p.o.) was used.

The results are shown in Table 2.

The tested compounds according to the invention show at least as good an anti-androgenic action on the seminal vesicles of the mouse as the comparison substances CPA and bicalutamide.

TABLE 2

Action of Selective Test Substances on the Testosterone-Stimulated Growth of the Seminal Vesicles.

| Example | Test Substance | % Inhibition of MSB Growth | Dose [mg/kg] |
|---|---|---|---|
| 1 | 4-[4,4-Dimethyl-5-oxo-3-[8-(pyrrolidin-1-yl)octyl]-2-thioxoimidazolidin-1-yl]-2-(trifluoromethyl)benzonitrile | 99 | 30 p.o. |
| | | 82 | 10 p.o. |
| 2 | 4-[4,4-Dimethyl-5-oxo-3-[8-(pyrrolidin-1-yl)octyl]-2-thioxoimidazolidin-1-yl]-2-(trifluoromethyl)benzonitrile hydrochloride | 95 | 30 p.o. |

TABLE 2-continued

Action of Selective Test Substances on the Testosterone-Stimulated Growth of the Seminal Vesicles.

| Example | Test Substance | % Inhibition of MSB Growth | Dose [mg/kg] |
| --- | --- | --- | --- |
| 10 | 4-[3-[8-[(2R)-2-(Hydroxymethyl)pyrrolidin-1-yl]octyl]-4,4-dimethyl-5-oxo-2-thioxoimidazolidin-1-yl]-2-(trifluoromethyl)benzonitrile | 87 | 10 p.o. |
| 11 | 4-[3-[8-[(2S)-2-(Hydroxymethyl)pyrrolidin-1-yl]octyl]-4,4-dimethyl-5-oxo-2-thioxoimidazolidin-1-yl]-2-(trifluoromethyl)benzonitrile | 95 | 30 p.o. |
| CPA | 17-(Acetyloxy)-6-chloro-1β,2β-dihydro-3'H-cyclopropa[1,2]pregna-1,4,6-triene-3,20-dione | 85 | 30 s.c. |
| Bicalutamide | N-[4-Cyano-3-(trifluoromethyl)phenyl]-3-[(4-fluorophenyl)sulfonyl]-2-hydroxy-2-methylpropanamide | 86 82 | 30 s.c. 30 p.o. |

Model 3: Anti-Androgenic Action of a Selective Test Substance on the Growth of Human Prostate Cancer Xenografts In Vivo In this invention, the action of Example 1 according to the invention: 4-[4,4-dimethyl-5-oxo-3-[8-(pyrrolidin-1-yl)octyl]-2-thioxoimidazolidin-1-yl]-2-(trifluoromethyl)benzonitrile, 11: 4-[3-[8-[(2S)-2-(hydroxymethyl)pyrrolidin-1-yl]octyl]-4,4-dimethyl-5-oxo-2-thioxoimidazolidin-1-yl]-2-(trifluoromethyl)benzonitrile and 23: 4-[3-[7-(3-hydroxy-8-azabicyclo[3.2.1]oct-8-yl)heptyl]-4,4-dimethyl-5-oxo-2thioxoimidazolidin-1-yl]-2-(trifluoromethyl)benzonitrile on the tumor growth in vivo was studied by means of mouse-xenograft models, in which the compounds according to the invention were administered 1× daily.

The CWR22 tumor model [M. A. Wainstein, F. He, D. Robinson, H. J. Kung, S. Schwartz, J. M. Giaconia, N. L. Edgehouse, T. P. Pretlow, D. R. Bodner, E. D. Kursh, Cancer Res. 1994, 1; 54(23), 6049–52] is a hormone-dependent human prostate cancer model. The tumor model was established in immunodeficient hairless mice and further propagated by "serial passaging" of prostate cancer tissue, which was removed during an OP. The androgen-dependent LNCaP prostate cancer model was also established by a patient tumor. This tumor model grows both in cell culture and as a xenotransplant in immunodeficient mice (Culig, Hoffmann *Brit. J Cancer,* 1999, 242–251). For therapy tests, 6-week-old male hairless mice (NMRI-Maus, M&B, Bomholdtgard, Denmark) were supplemented with testosterone pellets (12.5 mg, 90-day release, IRA, Sarasota, Fla.). In the animals, either LNCaP cells ($1.5 \times 10^6$ cells) or small CWR22 tumor fragments (2×2 mm) were implanted subcutaneously in the left side. After the tumors reached a size of 20–25 $mm^2$, treatment was begun with the invention substance. [M. A. Wainstein, F. He, D. Robinson, H. J. Kung, S. Schwartz, J. M. Giaconia, N. L. Edge-house, T. P. Pretlow, D. R. Bodner, E. D. Kursh, *Cancer Res.* 1994, 1; 54(23), 6049–52].

The results are shown in FIGS. 1–4.

BRIEF DESCRIPTION OF DRAWINGS

according to Example 23.
Figure 1. Growth inhibition of LNCaP prostate cancers by substance according to Example 1. The treatment was carried out 1 x daily p.o. with 10 mg/kg. For comparison, bicalutamide as a reference substance was administered 1 x daily at 30 mg/kg.
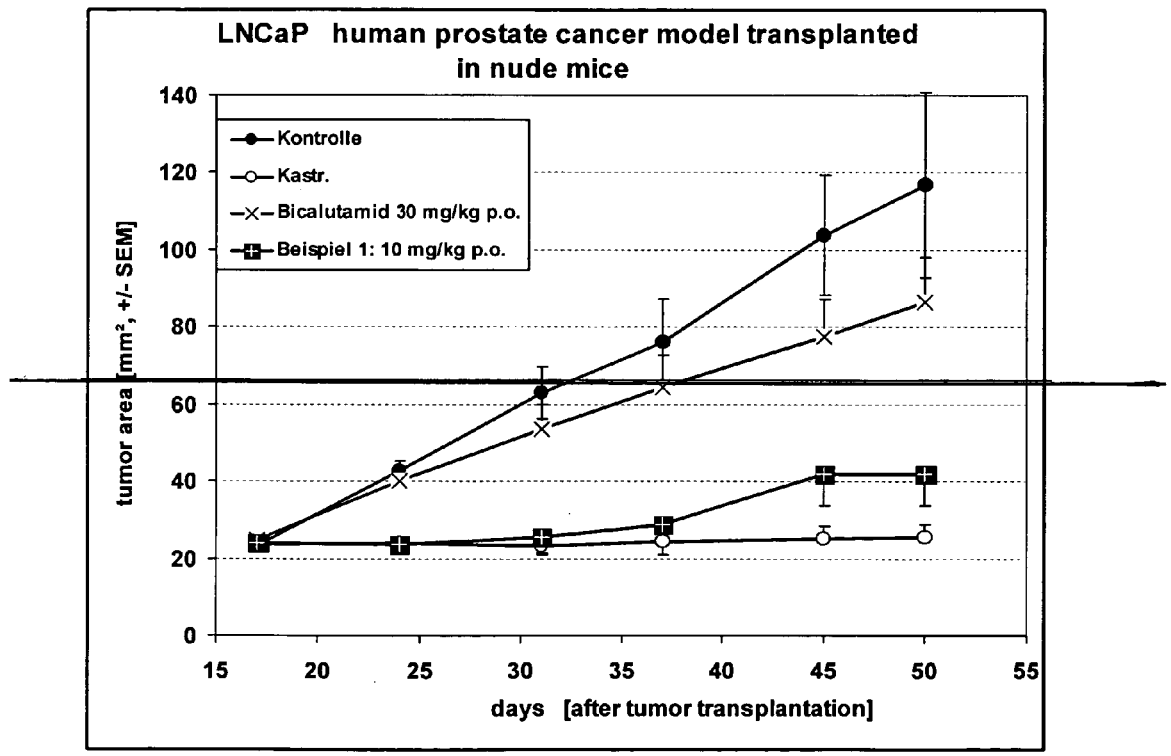
Key to Figure 1:
Kontrolle = Control Kastr. = Castr.
Bicalutamid = Bicalutamide
Beispiel = Example
Diagram Figure 2. Growth inhibition of CWR22 prostate cancers by substance according to Example 1. The treatment was carried out 1 x daily p.o. with 30 mg/kg. For comparison, bicalutamide as a reference substance was administered 1 x daily at 30 mg/kg.
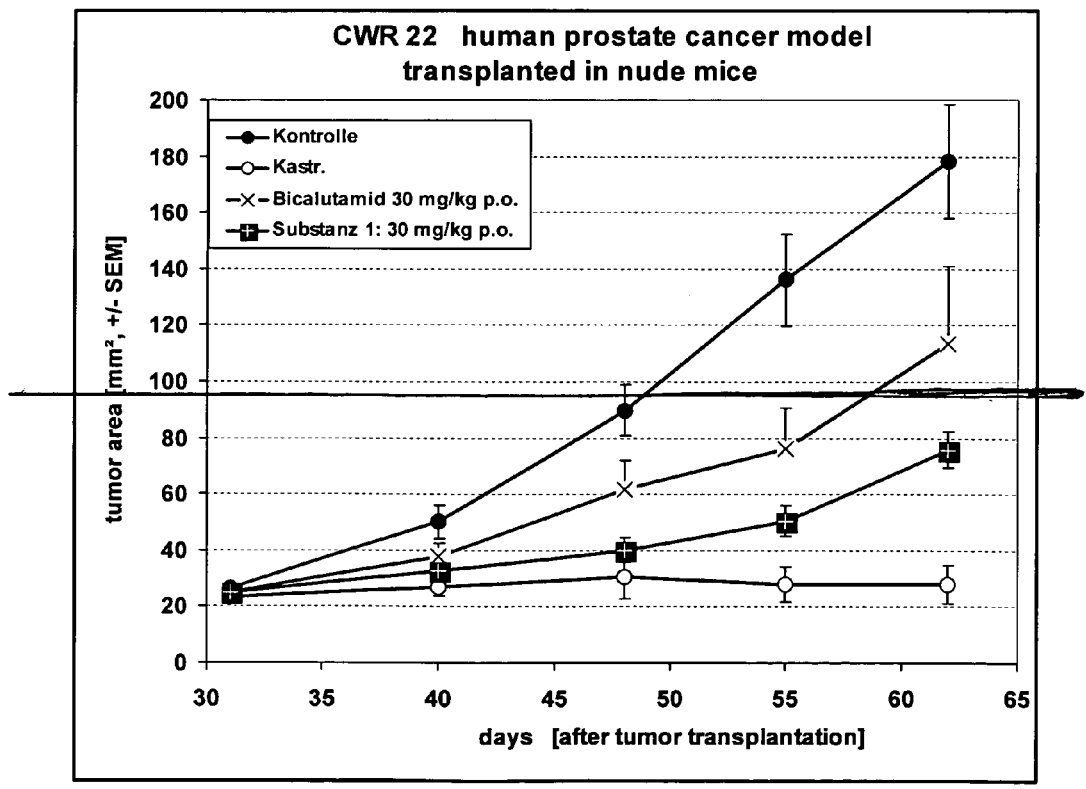

Figure 2:
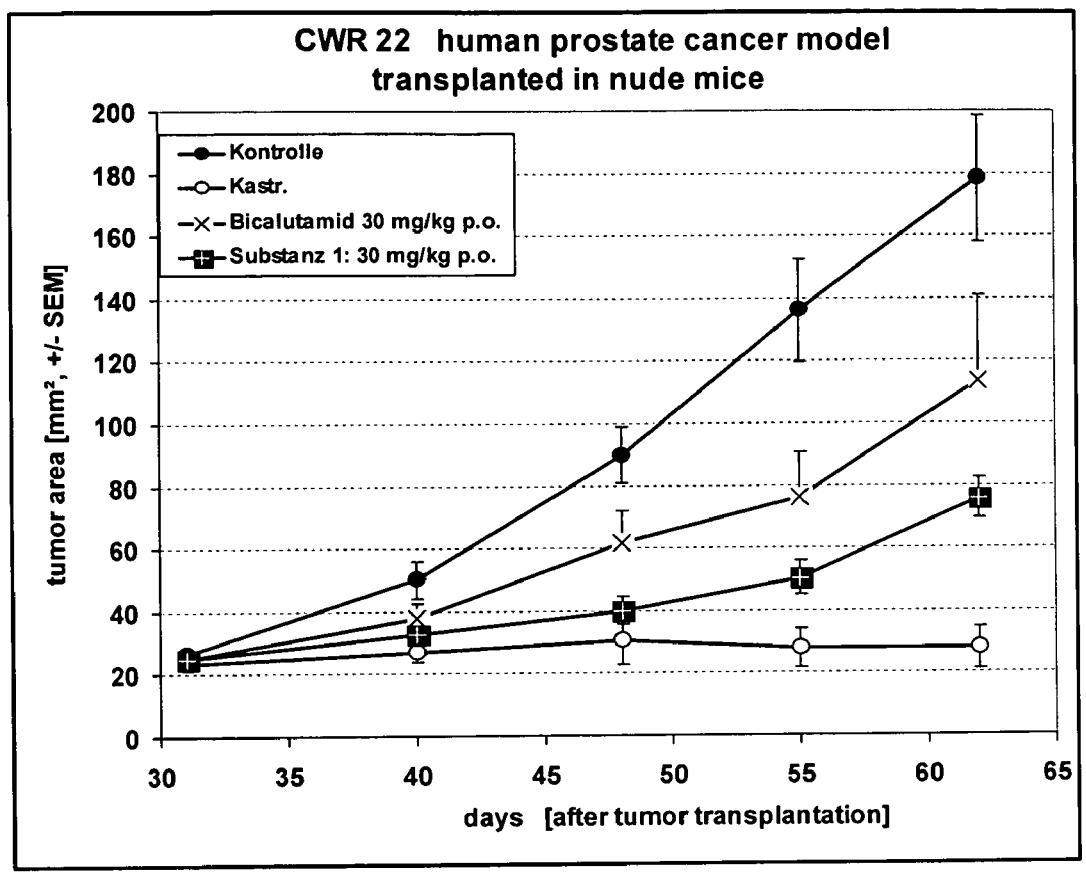
FIG. 2 illustrates results for growth inhibition of CWR22 prostate cancers by substance according to Example 1.

[Key:] Key to Figure 2:

Kontrolle = Control

Kastr. = Castr.

Bicalutamid = Bicalutamide

Substanz = Substance

While the tumor grows quickly in the untreated control animals, treatment with the compounds according to the invention results in a considerable growth inhibition of the prostate tumors, which is more strongly pronounced than in the animals that are treated with bicalutamide. Both in the LNCaP tumor and in the CWR22 tumor, this growth inhibition is comparable to the effects of castration (Diagrams Figures 1–2).

Figure 3:
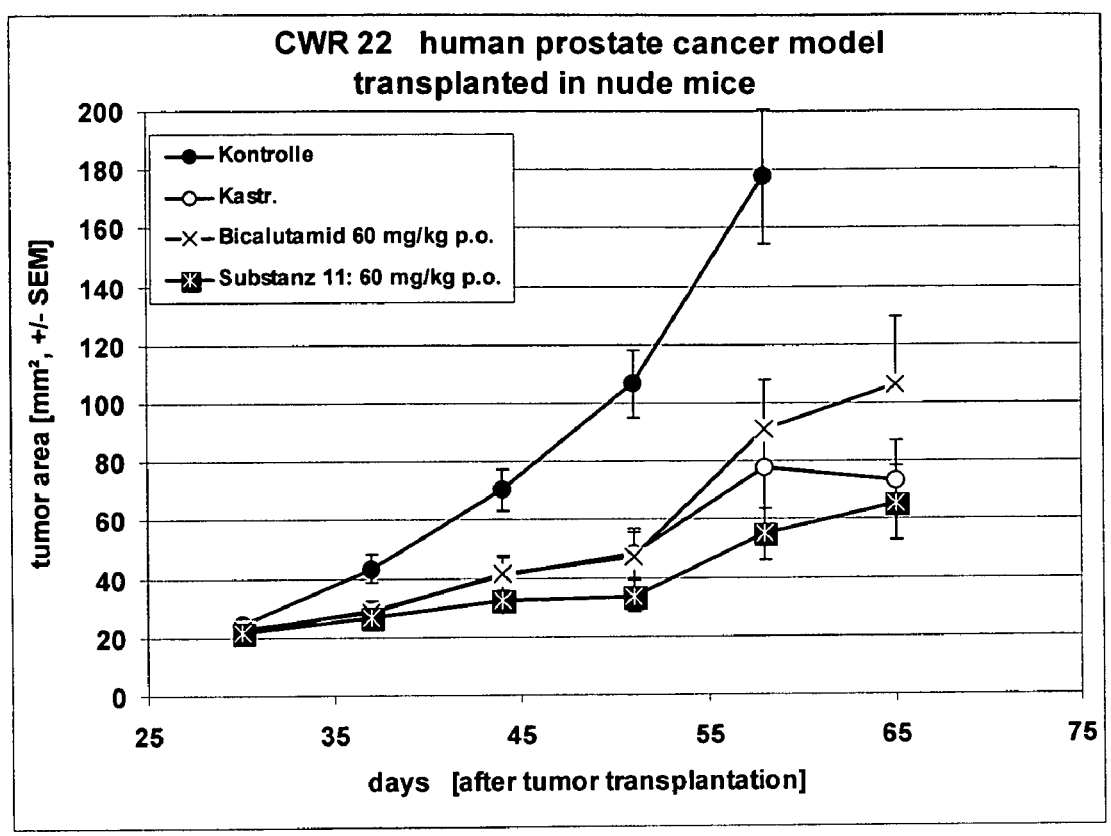
FIG. 3 illustrates results for growth inhibition of CWR22 prostate cancers by substance according to Example 11.

Diagram Figure 3. Growth inhibition of CWR22 prostate cancers by substance according to Example 11. The treatment was carried out 1 x daily p.o. with 60 mg/kg. For comparison, bicalutamide as a reference substance was administered 1 x daily at 60 mg/kg.

Figure 1:
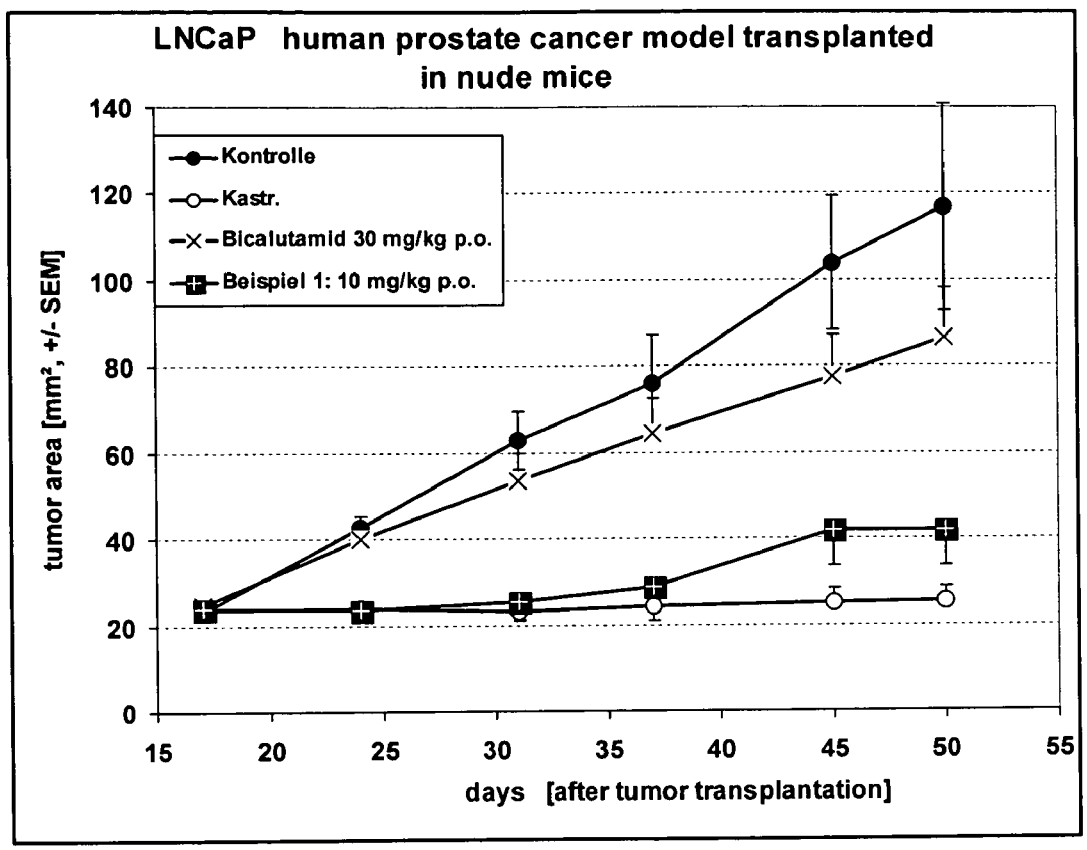
FIG. 1 illustrates results for growth inhibition of LNCaP prostate cancers by substance according to Example 1.

While the tumor grows quickly in the untreated control animals, treatment with the compounds according to the invention results in a considerable growth inhibition of the prostate tumors, which is more strongly pronounced than in the animals that are treated with bicalutamide. Both in the LNCaP tumor and in the CWR22 tumor, this growth inhibition is comparable to the effects of castration (FIGS. 1–2).

[Key:] Key to Figure 2:

Kontrolle = Control

Kastr. = Castr.

Bicalutamid = Bicalutamide

Substanz = Substance

While the tumor grows quickly in the untreated control animals, treatment with the compounds according to the invention results in a considerable growth inhibition of the prostate tumors, which is more strongly pronounced than in the animals that are treated with bicalutamide. Both in the LNCaP tumor and in the CWR22 tumor, this growth inhibition is comparable to the effects of castration (Diagrams Figures 1–2).

Diagram Figure 3. Growth inhibition of CWR22 prostate cancers by substance according to Example 11. The treatment was carried out 1 x daily p.o. with 60 mg/kg. For comparison, bicalutamide as a reference substance was administered 1 x daily at 60 mg/kg.

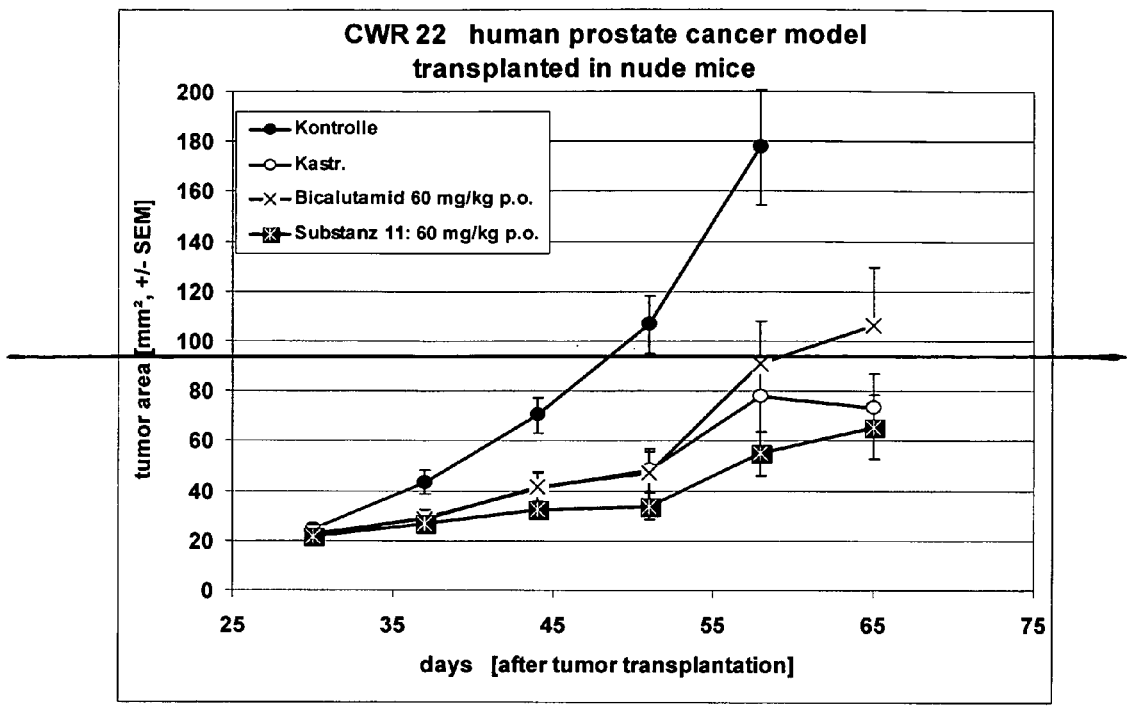

Key to Figure 3:

Kontrolle = Control

Kastr. = Castr.

Bicalutamid = Bicalutamide

Substanz = Substance

While the tumor grows quickly in the untreated control animals, treatment with the compounds according to the invention results in a significant growth inhibition of the prostate tumors. In this experiment, the growth inhibition of the CWR22-prostate cancer is comparable to FIG. 3. Growth inhibition of CWR22 prostate cancers by substance according to Example 11. The treatment was carried out 1× daily p.o. with 60 mg/kg. For comparison, bicalutamide as a reference substance was administered 1× daily at 60 mg/kg.

Figure 4:
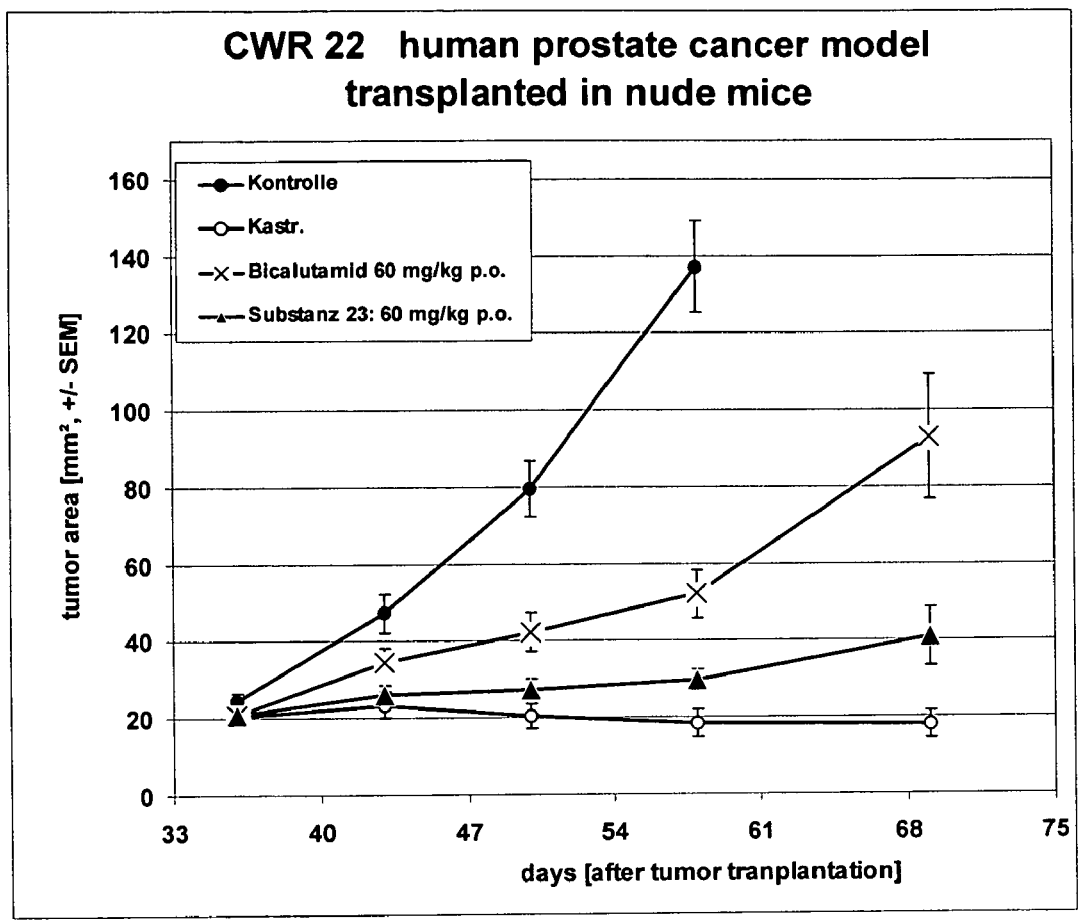
FIG. 4 illustrates results for growth inhibition of CWR22 prostate cancers by substance according to Example 23.

While the tumor grows quickly in the untreated control animals, treatment with the compounds according to the invention results in a significant growth inhibition of the prostate tumors. In this experiment, the growth inhibition of the CWR22-prostate cancer is comparable to the effects of castration (FIG. 3).

the effects of castration (~~Diagram~~ Figure 3).
~~Diagram~~ Figure 4. Growth inhibition of CWR22 prostate cancers by substance according to Example 23. The treatment was carried out 1 x daily p.o. with 60 mg/kg. For comparison, bicalutamide as a reference substance was administered 1 x daily at 60 mg/kg.
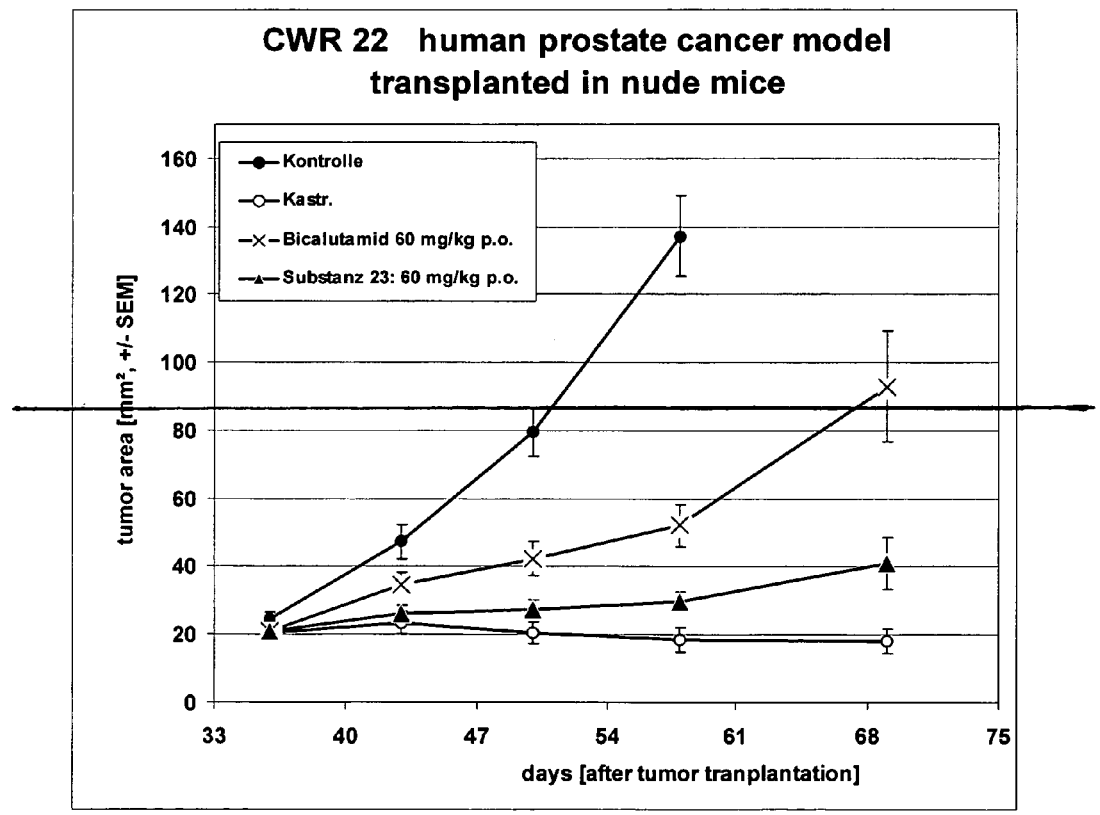
~~[Key:]~~ Key to Figure 4:
Kontrolle = Control Kastr. = Castr.

Bicalutamid = Bicalutamide

Substanz = Substance

While the tumor grows quickly in the untreated control animals, treatment with the compounds according to the invention results in a significant growth inhibition of the prostate tumors. In this experiment, the growth inhibition of the CWR22-prostate cancer is comparable to the effects of castration and superior to the comparison substance bicalutamide (~~Diagram~~ Figure 4).

Synthesis Scheme ~~Diagram~~

Thiohydantoin derivatives of chain lengths n = 6 to 9 can be produced according to the following scheme ~~diagram~~:

FIG. 4. Growth inhibition of CWR22 prostate cancers by substance according to Example 23. The treatment was carried out 1× daily p.o. with 60 mg/kg. For comparison, bicalutamide as a reference substance was administered 1 daily at 60 mg/kg.

Key to FIG. 4:

Kontrolle=Control

Kastr.=Castr.

Bicalutamid=Bicalutamide

Substanz=Substance

While the tumor grows quickly in the untreated control animals, treatment with the compounds according to the invention results in a significant growth inhibition of the prostate tumors. In this experiment, the growth inhibition of the CWR22-prostate cancer is comparable to the effects of castration and superior to the comparison substance bicalutamide (FIG. 4).

While the tumor grows quickly in the untreated control animals, treatment with the compounds according to the invention results in a significant growth inhibition of the prostate tumors. In this experiment, the growth inhibition of the CWR22-prostate cancer is comparable to the effects of castration (FIG. 3).

In this invention, the action of the compounds according to the invention on tumor growth in vivo was studied by means of two different mouse-xenograft models, in which the compounds according to the invention were orally administered 1× daily over the entire treatment period. In comparison to the untreated control animals, an inhibition of the tumor growth resulted. Retardation of the tumor growth was shown as significant in castrated mice. The treatment was well tolerated.

In both models (CWR22; LNCaP), the inhibition of the tumor growth by the compounds according to the invention is superior to the treatment with the anti-androgen bicalutamide.

Model 4: Pharmacokinetics in Rats After Intravenous and Peroral Administration

The pharmacokinetic properties of the compounds according to the invention were studied in Examples 1: 4-[4,4-dimethyl-5-oxo-3-[8-(pyrrolidin-1-yl)octyl]-2-thiox-oimidazolidin-1-yl]-2-(trifluoromethyl)benzonitrile and 11: 4-[3-[8-[(2S)-2-(hydroxymethyl)pyrrolidin-1-yl]octyl]-4,4-dimethyl-5-oxo-2-thioxoimidazolidin-1-yl]-2-(trifluoromethyl)benzonitrile.

TABLE 3

Pharmacokinetic Properties of Selected Examples

| Determined Parameters | Example 1 | Example 11 |
|---|---|---|
| Distribution Volume $V_{dss}$ [l/kg] | 37 | 11 |
| Systemic Serum Clearance CL [ml/min/kg] | 76 | 20 |
| Half-Life i.v. $T_{1/2}$ [h] | 5.6 | 5.7 |
| Half-Life p.o. $T_{1/2}$ [h] | 6.1 | 8.0 |
| Absorption $T_{max}$ [h] | 5 | 7 |
| Oral Bioavailability [%] | 72 | 65 |

The determined pharmacokinetic data show very advantageous pharmacokinetic properties of the compounds according to the invention in rats, which result in high oral bioavailability and a long half-life (>5 h). The data indicate a high intestinal absorption and a relatively low liver-first-pass-effect (increased metabolical stability).

Model 5: Destabilization of AR in LNCaP Cells by Test Substances

In a 25 cm$^2$ cell culture flask, 2×10$^6$ LNCaP cells in 6 ml of RPMI 1640 without phenol red are grown with 4 mmol of glutamine and 5% activated carbon-treated serum (CCS) and cultivated overnight at 37° C., 5% $CO_2$ in a humid atmosphere. On the next day, the cells are treated with the test substance at a concentration of 10 or 1 μmol, whereby the final concentration of the solvent is 0.5% DMSO. As a control, cells are treated only with 0.5% DMSO. After an incubation time of 24 hours, the medium is changed with renewed administration of substance, and another 24 hours of incubation. After 48 hours, the cells are washed with PBS, dissolved with PBS/20 mmol of EDTA, washed again with PBS-Ca$^{2+}$/Mg$^{2+}$ and then frozen for at least 2 hours as a cell pellet at −80° C. Then, the cell pellet is resuspended in 200 μl of lysis buffer (50 mmol of tris/HCl, pH 7.5; 150 mmol of NaCl, 1.5 mmol of $MgCl_2$, 0.2% SDS, 10% glycerol, 1 mmol of DTT, 0.01× complete-EDTA protease inhibitors (Roche, Mannheim)) and treated with 10 U benzonase (Merck, Darmstadt) for 10 minutes at 4° C. After 5 mmol of EDTA is added, insoluble material is pelletized and 25 μg of the cell extract is separated in a 4–12% SDS-polyacrylamide gel (invitrogen). Then, the proteins are transferred to nitrocellulose (HyBondECL, Amersham) and incubated with monoclonal antibodies against the androgen receptor (AR441; Santa Cruz Biotechnologies; 1:400 dilution) and actin (ICN, 1:5000–1:20000 dilution). After incubation with the secondary antibody (anti mouse IgG-HRP, Amersham or -AP, invitrogen,), the Western Blot is developed by means of chemiluminescence (ECL, Amersham; Western Breeze, invitrogen), and the light signals are quantified with a ChemiImager™ (Kodak). The amount of androgen receptor is calculated in a ratio to actin as a percentage of the DMSO control.

Table 4 shows the action of selected test substances at concentrations of 10 or 1 μmol on the content of androgen receptor protein in the human prostate cell line LNCaP. The data correspond to the proportion, in percent, of the AR content of cells that were treated only with the solvent DMSO (=control). The treatment of the cells with the cited test substances results, as in Example 56 (4-[3-[7-[(2S)-4,4-dimethyl-5-oxo-2-(pyrrolidin-1-ylmethyl)pyrrolidin-1-yl]heptyl]-2-thioxoimidazolidin-1-yl]-2-trifluoromethyl)benzonitrile) at a treatment concentration of 1 μmol, in a reduction of the AR content to up to one-fourth of the control (24%). The comparison substance bicalutamide does not influence the AR content, while the synthetic androgen R1881 stabilizes the AR protein. The latter is known from the literature (J. A. Kemppainen. et. al. J. Biol. Chem. 1992, 267, 968–974).

By the reduction of the AR content, which presumably is carried out by a destabilization of the AR protein, the inhibitory action of the antihormones on cell proliferatoin is to be enhanced.

TABLE 4

AR Content (%) in LNCaP Cells After Treatment with Selected Test Substances

| Example | Test Substance | AR Content [%] at 10 μM | at 1 μM |
|---|---|---|---|
| 1 | 4-[4,4-Dimethyl-5-oxo-3-[8-(pyrrolidin-1-yl)octyl]-2-thioxoimidazolidin-1-yl]-2-(trifluoromethyl)-benzonitrile | 63 | |
| 2 | 4-[4,4-Dimethyl-5-oxo-3-[8-(pyrrolidin-1-yl)octyl]-2-thioxoimidazolidin-1-yl]-2-(trifluoromethyl)-benzonitrile hydrochloride | 50 | |
| 9 | 4-[3-[7-[(2S)-2-(Hydroxymethyl)pyrrolidin-1-yl]heptyl]-4,4-dimethyl-5-oxo-2-thioxoimidazolidin-1-yl]-2-(trifluoromethyl)benzonitrile | | 63 |
| 11 | 4-[3-[8-[(2S)-2-(Hydroxymethyl)pyrrolidin-1-yl]octyl]-4,4-dimethyl-5-oxo-2-thioxoimidazolidin-1-yl]-2-(trifluoromethyl)benzonitrile | 50 | |
| 37 | 4-[3-[8-[(2R,5S)-rel-2,5-Dimethylpyrrolidin-1-yl]octyl]-4,4-dimethyl-5-oxo-2-thioxoimidazolidin-1-yl]-2-(trifluoromethyl)benzonitrile | | 57 |
| 40 | 4-[3-[8-[(2S)-2-(1-Hydroxy-1-methylethyl)pyrrolidin-1-yl]octyl]-4,4-dimethyl-5-oxo-2-thioxoimidazolidin-1-yl]-2-(trifluoromethyl)benzonitrile | | 40 |
| 52 | (R)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide | 36 | 74 |
| 56 | 4-[3-[7-[(2S)-4,4-Dimethyl-5-oxo-2-(pyrrolidin-1-ylmethyl)pyrrolidin-1-yl]heptyl]-2-thioxoimidazolidin-1-yl]-2-(trifluoromethyl)benzonitrile | | 24 |
| Comparison US Re. 35956 Example 71 | 4-[3-(2-Hydroxyethyl)-4,4-dimethyl-5-oxo-2-thioxoimidazolidin-1-yl]-2-(trifluoromethyl)-benzonitrile | 191 | 164 |
| Comparison US Re. 35956 Example 77 | 4-[3-(4-Hydroxybutyl)-4,4-dimethyl-5-oxo-2-thioxoimidazolidin-1-yl]-2-(trifluoromethyl)-benzonitrile | 180 | 230 |
| Bicalutamide | N-[4-Cyano-3-(trifluoromethyl)phenyl]-3-[(4-fluorophenyl)sulfonyl]-2-hydroxy-2-methylpropanamide | 100 | |
| R1881 (10 nM) | 17β-Hydroxy-17α-methylestra-4,9,11-trien-3-one | 250 | |

The compounds according to the invention are suitable for an extended effective treatment or prophylaxis of androgen-dependent diseases of the human or animal body. The compounds according to the invention are suitable especially for the treatment or prophylaxis of androgen-dependent proliferative diseases, in particular prostate cancers and benign prostate hyperplasia (BHP).

This invention comprises pharmaceutical preparations that contain one or more compounds of general formula I or their pharmaceutically compatible salts, optionally together with pharmaceutically compatible adjuvants and/or vehicles, as well as the use of compounds of general formula I for the production of a pharmaceutical agent for treatment or prophylaxis of diseases of the human or animal body, which can be influenced by the inhibition of the androgen receptor.

In this sense, the compounds of general formula I according to the invention as well as pharmaceutical preparations that contain the latter can also be used for prophylaxis and/or therapy of other androgen-dependent images of disease or symptoms, which have a non-proliferative nature (e.g., androgenetic alopecia, hirsutism or androgen-dependent acne).

Dosage

In general, satisfactory results can be expected when the daily doses comprise a range of 5 μg to 50 mg of the compound according to the invention per kg of body weight. In the case of larger mammals, for example humans, a recommended daily dose is in the range of 10 μg to 30 mg per kg of body weight. Suitable dosages for the compounds according to the invention are from 0.005 to 50 mg per day per kg of body weight, depending on age and constitution of the patient, whereby the necessary daily dose can be administered one or more times.

The formulation of the pharmaceutical preparations based on the new compounds is carried out in a way that is known in the art by the active ingredient being administered with the vehicles, fillers, substances that influence decomposition, binding agents, moisturizers, lubricants, absorbents, diluents, flavoring correctives, coloring agents, etc., that are commonly used in galenicals and being converted into the desired form of administration. In this case, reference is made to Remington's Pharmaceutical Science, 15th ed. Mack Publishing Company, East Pennsylvania (1980).

For oral administration, in particular tablets, coated tablets, capsules, pills, powders, granulates, pastilles, suspensions, emulsions or solutions are suitable. For parenteral administration, injection and infusion preparations are possible. For intraarticulate injection, correspondingly prepared crystal suspensions can be used. For the intramuscular injection, aqueous and oily injection solutions or suspensions, and corresponding depot preparations can be used. For rectal administration, new compounds in the form of suppositories, capsules, solutions (e.g., in the form of enemas), and ointments can be used both for systemic and for local therapy. For topical application, formulations in gels, ointments, fatty ointments, creams, pastes, powders, milk, and tinctures are possible. The dosage of the compounds of general formula I should be 0.01%–20% in these preparations to achieve an adequate pharmacological action. The topical application can also be carried out by means of a transdermal system, for example a patch.

This invention comprises pharmaceutical compositions that contain at least one compound of general formula I or at least one of their pharmaceutically compatible salts, optionally together with pharmaceutically compatible adjuvants and/or vehicles.

These pharmaceutical compositions and pharmaceutical agents can be provided for oral, rectal, subcutaneous, transdermal, percutaneous, intravenous or intramuscular administration. In addition to the commonly used vehicles and/or diluents, they contain at least one compound of general formula I.

The pharmaceutical agents according to this invention are produced with a suitable dosage in a known way with the commonly used solid or liquid vehicles or diluents and the commonly used pharmaceutical-technical adjuvants according to the desired type of administration. The preferred preparations consist of a form for dispensing that is suitable for oral administration. Such forms for dispensing are, for example, tablets, film tablets, coated tablets, capsules, pills, powders, solutions or suspensions or else depot forms. The pharmaceutical compositions that contain at least one of the compounds according to the invention are preferably administered orally.

Parenteral preparations, such as injection solutions, can also be considered. In addition, for example, suppositories an also be mentioned as preparations.

Corresponding tablets can be obtained by, for example, mixing the active ingredient with known adjuvants, for example inert diluents such as dextrose, sugar, sorbitol, mannitol, polyvinyl pyrrolidone, explosives such as corn starch or alginic acid, binding agents such as starch or gelatin, lubricants such as magnesium stearate or talc and/or agents for achieving a depot effect such as carboxylpolymethylene, carboxylmethyl cellulose, cellulose acetate phthalate or polyvinyl acetate. The tablets can also consist of several layers.

Coated tablets accordingly can be produced by coating cores, which are produced analogously to the tablets, with agents that are commonly used in tablet coatings, for example polyvinyl pyrrolidone or shellac, gum arabic, talc, titanium oxide or sugar. In this case, the shell of the coated tablet can also consist of several layers, whereby the adjuvants that are mentioned above in the tablets can be used. In addition, solutions or suspensions with the compounds of general formula I according to the invention can contain taste-improving agents such as saccharine, cyclamate or sugar, as well as, e.g., flavoring substances such as vanilla or orange extract.

In addition, they can contain suspending adjuvants such as sodium carboxymethyl cellulose or preservatives such as p-hydroxybenzoates.

The capsules that contain compounds of general formula I can be produced, for example, by the compound(s) of general formula I being mixed with an inert vehicle such as lactose or sorbitol and encapsulated in gelatin capsules.

Suitable suppositories can be produced by, for example, mixing with vehicles that are provided for this purpose, such as neutral fats or polyethylene glycol or derivatives thereof.

For therapy and/or prophylaxis of androgen-dependent proliferative diseases, such as, for example, prostate cancers or benign prostate hyperplasia, the compounds according to the invention can be administered combined with one or more of the following active ingredients:

1) Gonadotropic hormone (GnRH) agonists
2) 5α-Reductase inhibitors such as finasteride
3) Cytostatic agents
4) VEGF-Kinase inhibitors
5) Antigestagens
6) Antiestrogens
7) Antisense oligonucleotides
8) EGF Antibodies
9) Estrogens It is also possible, in the treatment of prostate cancer with the compounds according to the invention, to combine their use with a method of clinical radiology that is known in the art (Laverdiere, J. et al., 1997, Intl. J. of Rad. Onc. Biol. Phys., 37, 247–252; Bolla, M. et al., 1997, New Engl. J. Med., 337, 95–300.) The compounds of general formula I according to the invention can be produced as described below.

This invention is explained in more detail based on the subsequent examples without being limited thereto.

Synthesis Scheme

Thiohydantoin derivatives of chain lengths n=6 to 9 can be produced according to the following scheme:

-continued

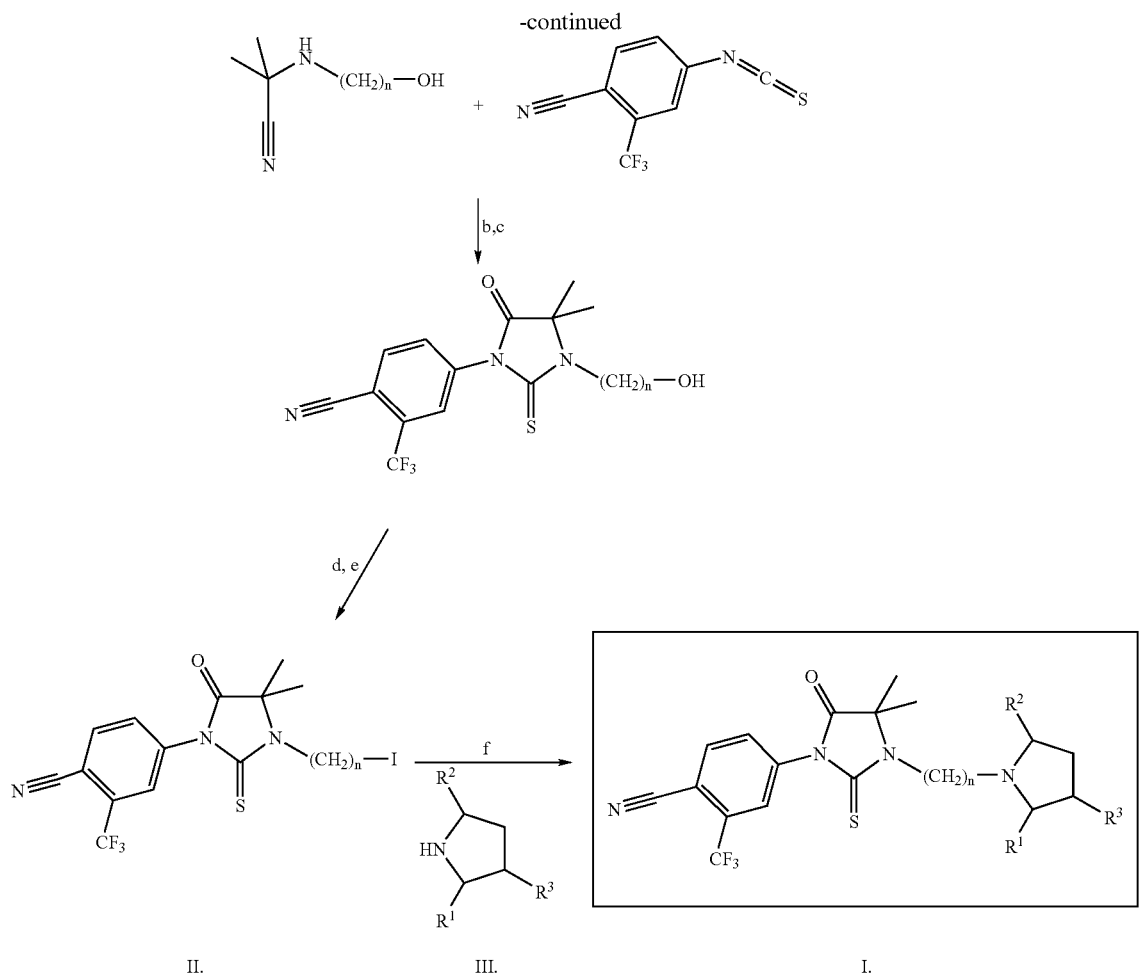

Reagents. (a) CSCl$_2$, DMF; (b) NEt$_3$, THF; (c) 4M HCl; (d) RSO$_2$Cl, NEt$_3$, CH$_2$Cl$_2$; (e) NaI, acetone; (f) NEt$_3$, THF.

Production Processes

EXAMPLE 1

4-[4,4-Dimethyl-5-oxo-3-[8-(pyrrolidin-1-yl)octyl]-2-thioxoimidazolidin-1-yl]-2-(trifluoromethyl)benzonitrile 1a) 8-Bromooctan-1-ol 25 g of octane-1,8-diol was boiled in 250 ml of cyclohexane with 22.6 ml of 47% aqueous hydrobromic acid for six hours in a water separator. The reaction mixture was then poured onto saturated aqueous sodium bicarbonate solution and extracted with ethyl acetate. The organic phase was washed with saturated, aqueous sodium chloride solution, dried on sodium sulfate, filtered and concentrated by evaporation in a vacuum. Column chromatography on silica gel with a mixture that consists of hexane/ethyl acetate yielded 21.6 g of the title compound as a yellowish oil.

$^1$H-NMR (300 MHz, CDCl$_3$): δ [ppm]=3.64 t (J=6.8 Hz, 2H, CH$_2$OH); 3.41 t (J=6.8 Hz, 2H, CH$_2$Br); 1.85 tt (J=7.3 Hz/6.8 Hz, 2H, CH$_2$); 1.56 m (2H, CH$_2$); 149–1.27 m (8H, CH$_2$).

1b) 2-(8-Hydroxyoctyl)-1H-isoindole-1,3(2H)-dione

A solution of 15.12 g of phthalic acid imide in 480 ml of N,N-dimethylformamide was mixed in portions at room temperature with 5.04 g of 50% sodium hydride as a dispersion in mineral oil. The reaction mixture was stirred for one hour at room temperature. Then, a solution of 20 g of the compound, produced under 1a), in 480 ml of N,N-dimethylformamide was added in drops, and the reaction mixture was stirred for three hours at room temperature. The mixture was then poured onto saturated aqueous sodium bicarbonate solution and extracted with ethyl acetate. The organic phase was washed with saturated aqueous sodium chloride solution, dried on sodium sulfate, filtered and concentrated by evaporation in a vacuum. Column chromatography on silica gel with a mixture that consists of hexane/ethyl acetate yielded 23.0 g of the title compound as a colorless foam.

$^1$H-NMR (300 MHz, CDCl$_3$): δ [ppm]=7.84 m (2H, aryl); 7.71 m (2H, aryl); 3.68 t (J=7 Hz, 2H, CH$_2$N); 3.62 t (J=6 Hz, 2H, CH$_2$OH); 1.67 m (2H, CH$_2$); 1.56 nm (2H, CH$_2$); 1.32 m (8H, CH$_2$).

1c) 8-Aminooctan-1-ol 15.2 ml of 80% aqueous hydrazinium hydroxide was added in drops to a solution of 23 g of the compound, produced under 1b), in 400 ml of ethanol. The reaction mixture was boiled for four hours. The white precipitate was filtered off and rewashed with ethanol. The filtrate was concentrated by evaporation in a vacuum. The residue was taken up in ethyl acetate and irradiated for 30 minutes in an ultrasound bath. The white precipitate was in turn filtered off and rewashed with ethyl acetate. The filtrate was concentrated by evaporation in a vacuum. 8.88 g of the title compound was obtained.

$^1$H-NMR (300 MHz, CDCl$_3$): δ [ppm]=3.62 t (J=7 Hz, 2H, CH$_2$OH); 2.68 t (J=6 Hz, 2H, CH$_2$NH$_2$); 1.56 m (2H, CH$_2$); 1.32 m (10H, CH$_2$).

1d) 4-[4,4-Dimethyl-5-oxo-3-(8-hydroxyoctyl)-2-thioxoimidazolidin-1-yl]-2-(trifluoromethyl)benzonitrile While being cooled in an ice bath and under nitrogen atmosphere, 2.3 ml of thiophosgene was added in drops to a solution of 4.99 g of 4-amino-2-(trifluoromethyl)benzonitrile in 30 ml of N,N-dimethylformamide. The reaction mixture was stirred for one hour at room temperature and then mixed with water. The aqueous phase was extracted with ethyl acetate. The combined organic phases were washed with saturated aqueous sodium chloride solution, dried on sodium sulfate, filtered and concentrated by evaporation in a vacuum. The thus obtained crude isothiocyanate was combined with the cyanamine produced by two hours of stirring of 5.4 ml of acetone cyanohydrin with 4.29 g of the compound produced under 1c) in the presence of 3 g of molecular sieve 3 Å at room temperature and boiled for one hour with 7.47 ml of triethylamine in 134 ml of tetrahydrofuran. The crude iminothiohydantoin obtained after concentration by evaporation in a vacuum was stirred with 26.8 ml of 4 molar aqueous hydrochloric acid in 134 ml of methanol overnight at room temperature. The reaction mixture was then poured onto saturated aqueous sodium bicarbonate solution and extracted with ethyl acetate. The organic phase was washed with saturated aqueous sodium chloride solution, dried on sodium sulfate, filtered and concentrated by evaporation in a vacuum. Column chromatography on silica gel with a mixture that consists of hexane/ethyl acetate yielded 8.1 g of the title compound as a colorless foam.

$^1$H-NMR (300 MHz, CDCl$_3$): δ [ppm]=7.94 d (J=8 Hz, 1H, aryl); 7.89 d (J=2.1 Hz, 1H, aryl); 7.77 dd (J=8 Hz/2.1 Hz, 1H, aryl); 3.67 m (2H, CH$_2$N); 3.65 t (J=6.5 Hz, 2H, CH$_2$OH); 1.83 m (2H, CH$_2$); 1.55 m (2H, CH$_2$); 1.58 s (6H, CH$_3$); 1.37 m (8H, CH$_2$).

1e) 8-[3-[4-Cyano-3-(trifluoromethyl)phenyl]-5,5-dimethyl-4-oxo-2-thioxoimidazolidin-1-yl]octyl 4-methylbenzenesulfonate 8.1 g of the compound produced under 1d) was stirred for one hour at room temperature with 21.0 g of p-toluenesulfonic acid chloride and 25.5 ml of triethylamine in 92 ml of dichloromethane. The reaction mixture was poured into saturated, aqueous sodium bicarbonate solution and extracted with dichloromethane. The organic phase was washed with saturated, aqueous sodium chloride solution, dried on sodium sulfate, filtered and concentrated by evaporation in a vacuum. Column chromatography on silica gel with a mixture that consists of hexane/ethyl acetate yielded 9.21 g of the title compound as a colorless foam.

$^1$H-NMR (300 MHz, CDCl$_3$): δ [ppm]=7.94 d (J=8 Hz, 1H, aryl); 7.89 d (J=2.1 Hz, 1H, aryl); 7.78 d (J=8.2 Hz, 2H, aryl); 7.77 dd (J=8 Hz/2.1 Hz, 1H, aryl); 7.34 d (J=8.2 Hz, 2H, aryl); 4.03 t (J=6.5 Hz, 2H, CH$_2$O); 3.66 m (2H, CH$_2$N); 2.45 s (3H, CH$_3$); 1.81 m (2H, CH$_2$); 1.65 m (2H, CH$_2$); 1.58 s (6H, CH$_3$); 1.33 m (8H, CH$_2$).

1f) 4-[4,4-Dimethyl-5-oxo-3-(8-iodooctyl)-2-thioxoimidazolidin-1-yl]-2-(trifluoromethyl)benzonitrile 9.21 g of the compound produced under 1e) was boiled for one hour with 9.3 g of sodium iodide in 150 ml of acetone. The reaction mixture was filtered at room temperature and concentrated by evaporation in a vacuum. Column chromatography on silica gel with a mixture that consists of hexane/ethyl acetate yielded 8.55 g of the title compound as a yellowish foam.

$^1$H-NMR (300 MHz, CDCl$_3$): δ [ppm]=7.95 d (J=8 Hz, 1H, aryl); 7.89 d (J=2.1 Hz, 1H, aryl); 7.77 dd (J=8 Hz/2.1 Hz, 1H, aryl); 3.67 m (2H, CH$_2$N); 3.20 t (J=7 Hz, 2H, CH$_2$I); 1.82 m (2H, CH$_2$); 1.80 m (2H, CH$_2$); 1.58 s (6H, CH$_3$); 1.37 m (8H, CH$_2$).

1g) 4-[4,4-Dimethyl-5-oxo-3-[8-(pyrrolidin-1-yl)octyl]-2-thioxoimidazolidin-1-yl]-2-(trifluoromethyl)benzonitrile 200 mg of the compound produced under 1f) was boiled for four hours with 60 µl of pyrrolidine and 101 µl of triethylamine in 5 ml of tetrahydrofuran. The reaction mixture was concentrated by evaporation in a vacuum. Column chromatography on silica gel with a mixture that consists of hexane/ethyl acetate yielded 130 mg of the title compound as a colorless oil.

$^1$H-NMR (300 MHz, CDCl$_3$): δ [ppm]=7.94 d (J=8 Hz, 1H, aryl); 7.89 d (J=2.1 Hz, 1H, aryl); 7.77 dd (J=8 Hz/2.1 Hz, 1H, aryl); 3.67 m (2H, CH$_2$N); 2.64 m (4H, CH$_2$N); 2.53 m (2H, CH$_2$N); 1.85 m (4H, CH$_2$); 1.82 m (2H, CH$_2$); 1.59 m (2H, CH$_2$); 1.58 s (6H, CH$_3$); 1.36 m (8H, CH$_2$).

EXAMPLE 2

4-[4,4-Dimethyl-5-oxo-3-[8-(pyrrolidin-1-yl)octyl]-2-thioxoimidazolidin-1-yl]-2-(trifluoromethyl)benzonitrile hydrochloride 20 mg of the compound, produced under 1 g), was dissolved in 1 ml of tetrahydrofuran and stirred for one hour at room temperature with 67 µl of a 1.2 molar solution of hydrochloric acid in diethyl ether. The reaction mixture was concentrated by evaporation in a vacuum. 21 mg of the title compound was obtained.

$^1$H-NMR (300 MHz, CDCl$_3$): δ [ppm]=7.95 d (J=8 Hz, 1H, aryl); 7.89 d (J=2.1 Hz, 1H, aryl); 7.78 dd (J=8 Hz/2.1 Hz, 1H, aryl); 3.79 m (2H, CH$_2$N); 3.67 m (2H, CH$_2$N); 3.00 m (2H, CH$_2$N); 2.75 m (2H, CH$_2$N); 2.23 m (2H, CH$_2$); 2.06 m (2H, CH$_2$); 1.90 m (2H, CH$_2$); 1.82 m (2H, CH$_2$); 1.59 s (6H, CH$_3$); 1.38 m (8H, CH$_2$).

EXAMPLE 3

4-[4,4-Dimethyl-5-oxo-3-[6-(pyrrolidin-1-yl)hexyl]-2-thioxoimidazolidin-1-yl]-2-(trifluoromethyl)benzonitrile 3a) 4-[3-(6-Iodohexyl)-4,4-dimethyl-5-oxo-2-thioxoimidazolidin-1-yl]-2-(trifluoromethyl)benzonitrile The production of the title compound was carried out analogously to the process described in Examples 1d) to 1f). 6-Aminohexan-1-ol was used as a chain component.

¹H-NMR (300 MHz, CDCl₃): δ [ppm]=7.95 d (J=8 Hz, 1H, aryl); 7.89 d (J=2.1 Hz, 1H, aryl); 7.77 dd (J=8 Hz/2.1 Hz, 1H, aryl); 3.68 m (2H, CH₂N); 3.21 t (J=6.8 Hz, 2H, CH₂I); 1.86 m (2H, CH₂); 1.83 m (2H, CH₂); 1.59 s (6H, CH₃); 1.46 m (4H, CH₂).

3b) 4-[4,4-Dimethyl-5-oxo-3-[6-(pyrrolidin-1-yl)hexyl]-2-thioxoimidazolidin-1-yl]-2-(trifluoromethyl)benzonitrile 20 mg of the compound, produced under 3a), was boiled for four hours with 6.3 μl of pyrrolidine and 10.6 μl of triethylamine in 1 ml of tetrahydrofuran. The reaction mixture was concentrated by evaporation in a vacuum. Column chromatography on silica gel with a mixture that consists of hexane/ethyl acetate yielded 15 mg of the title compound as a colorless oil.

¹H-NMR (300 MHz, CDCl₃): δ [ppm]=7.95 d (J=8 Hz, 1H, aryl); 7.89 d (J=2.1 Hz, 1H, aryl); 7.77 dd (J=8 Hz/2.1 Hz, 1H, aryl); 3.68 m (2H, CH₂N); 2.75 m (4H, CH₂N); 2.64 m (2H, CH₂N); 1.90 m (4H, CH₂); 1.84 m (2H, CH₂); 1.68 m (2H, CH₂); 1.59 s (6H, CH₃); 1.43 m (4H, CH₂).

EXAMPLE 4

4-[4,4-Dimethyl-5-oxo-3-[7-(pyrrolidin-1-yl)heptyl]-2-thioxoimidazolidin-1-yl]-2-(trifluoromethyl)benzonitrile

4a) 4-[3-(7-Iodoheptyl)-4,4-dimethyl-5-oxo-2-thioxoimidazolidin-1-yl]-2-(trifluoromethyl)benzonitrile The production of the title compound was carried out analogously to the process described in Examples 1a) to 1f). As a chain component, heptane-1,7-diol was used.

¹H-NMR (300 MHz, CDCl₃): δ [ppm]=7.95 d (J=8 Hz, 1H, aryl); 7.90 d (J=2.1 Hz, 1H, aryl); 7.78 dd (J=8 Hz/2.1 Hz, 1H, aryl); 3.67 m (2H, CH₂N); 3.20 t (J=7 Hz, 2H, CH₂I); 1.84 m (4H, CH₂); 1.59 s (6H, CH₃); 1.41 m (6H, CH₂).

4b) 4-[4,4-Dimethyl-5-oxo-3-[7-(pyrrolidin-1-yl)heptyl]-2-thioxoimidazolidin-1-yl]-2-(trifluoromethyl)benzonitrile 13 mg of the compound produced under 4a) was boiled for four hours with 4 μl of pyrrolidine and 6.7 μl of triethylamine in 1 ml of tetrahydrofuran. The reaction mixture was concentrated by evaporation in a vacuum. Column chromatography on silica gel with a mixture that consists of hexane/ethyl acetate yielded 7 mg of the title compound as a colorless oil.

¹H-NMR (300 MHz, CDCl₃): δ [ppm]=7.95 d (J=8 Hz, 1H, aryl); 7.89 d (J=2.1 Hz, 1H, aryl); 7.78 dd (J=8 Hz/2.1 Hz, 1H, aryl); 3.67 m (2H, CH₂N); 2.72 m (4H, CH₂N); 2.60 m (2H, CH₂N); 1.89 m (4H, CH₂); 1.83 m (2H, CH₂); 1.65 m (2H, CH₂); 1.58 s (6H, CH₃); 1.40 m (6H, CH₂).

EXAMPLE 5

4-[4,4-Dimethyl-5-oxo-3-[9-(pyrrolidin-1-yl)nonyl]-2-thioxoimidazolidin-1-yl]-2-(trifluoromethyl)benzonitrile

5a) 4-[3-(9-Iodononyl)-4,4-dimethyl-5-oxo-2-thioxoimidazolidin-1-yl]-2-(trifluoromethyl)benzonitrile The production of the title compound was carried out analogously to the process described in Examples 1a) to 1f). Nonane-1,9-diol was used as a chain component.

¹H-NMR (300 MHz, CDCl₃): δ [ppm]=7.95 d (J=8 Hz, 1H, aryl); 7.89 d (J=2.1 Hz, 1H, aryl); 7.77 dd (J=8 Hz/2.1 Hz, 1H, aryl); 3.67 m (2H, CH₂N); 3.19 t (J=7 Hz, 2H, CH₂I); 1.84 m (2H, CH₂); 1.82 m (2H, CH₂); 1.58 s (6H, CH₃); 1.36 m (10H, CH₂).

5b) 4-[4,4-Dimethyl-5-oxo-3-[9-(pyrrolidin-1-yl)nonyl]-2-thioxoimidazolidin-1-yl]-2-(trifluoromethyl)benzonitrile 20 mg of the compound produced under 5a) was boiled for four hours with 5.9 μl of pyrrolidine and 9.9 μl of triethylamine in 1 ml of tetrahydrofuran. The reaction mixture was concentrated by evaporation in a vacuum. Column chromatography on silica gel with a mixture that consists of hexane/ethyl acetate yielded 10 mg of the title compound as a colorless oil.

¹H-NMR (300 MHz, CDCl₃): δ [ppm]=7.95 d (J=8 Hz, 1H, aryl); 7.89 d (J=2.1 Hz, 1H, aryl); 7.77 dd (J=8 Hz/2.1 Hz, 1H, aryl); 3.66 m (2H, CH₂N); 2.47 m (4H, CH₂N); 2.40 m (2H, CH₂N); 1.77 m (4H, CH₂); 1.82 m (2H, CH₂); 1.58 s (6H, CH₃), 1.51 m (2H, CH₂); 1.31 m (10H, CH₂).

Analogously to the production instructions, described in detail, in Examples 1 to 5, the following compounds were obtained:

| Example | Product/Reagent | Instructions analagous to | ¹H-NMR(300 MHz, CDCl₃) δ [ppm] |
|---|---|---|---|
| 6 | 4-[3-[6-[(2R)-2-(Hydroxymethyl)-pyrrolidin-1-yl]hexyl]-4,4-dimethyl-5-oxo-2-thioxoimidazolidin-1-yl]-2-(trifluoromethyl)-benzonitrile (2R)-Pyrrolidine-methanol | 3 | 7.95d(J=8Hz, 1H, aryl); 7.90d(J=2.1Hz, 1H, aryl); 7.77dd(J=8Hz/2.1Hz, 1H, aryl); 3.67m(2H, CH₂N); 3.62dd (J=10.5Hz/3.8Hz, 1H, CH₂OH); 3.39 dd(J=10.5Hz/2.1Hz, 1H, CH₂OH); 3.19m(1H, CH₂N); 2.73dddbr(J=11.8Hz/7.6Hz/7.6Hz, 1H, CH₂N); 2.58 m(1H, CH₂N); 2.25m(2H, CH₂N); 1.96–1.67m(4H, CH₂); 1.84m(2H, CH₂); 1.58s(6H, CH₃); 1.54m(2H, CH₂); 1.41m(4H, CH₂) |
| 7 | 4-[3-[6-[(2S)-2-(Hydroxymethyl)-pyrrolidin-1-yl]hexyl]-4,4-dimethyl-5-oxo-2- | 3 | 7.95d(J=8Hz, 1H, aryl); 7.90d(J=2.1Hz, 1H, aryl); 7.77dd(J=8Hz/2.1Hz, 1H, aryl); 3.67m(2H, CH₂N); 3.62dd (J=10.5Hz/3.8Hz, 1H, CH₂OH); 3.39 |

-continued

| Example | Product/Reagent | Instructions analagous to | $^1$H-NMR(300 MHz, CDCl$_3$) δ [ppm] |
|---|---|---|---|
| | thioxoimidazolidin-1-yl]-2-(trifluoromethyl)-benzonitrile (2S)-Pyrrolidinemethanol | | dd(J=10.5Hz/2.1Hz, 1H, CH$_2$OH); 3.19m(1H, CH$_2$N); 2.73dddbr(J=11.8Hz/7.6Hz/7.6Hz, 1H, CH$_2$N); 2.58 m(1H, CH$_2$N); 2.25m(2H, CH$_2$N); 1.96–1.67m(4H, CH$_2$); 1.84m(2H, CH$_2$); 1.58s(6H, CH$_3$); 1.54m(2H, CH$_2$); 1.41m(4H, CH$_2$) |
| 8 | 4-[3-[7-[(2R)-2-(Hydroxymethyl)-pyrrolidin-1-yl]heptyl]-4,4-dimethyl-5-oxo-2-thioxoimidazolidin-1-yl]-2-(trifluoromethyl)-benzonitrile (2R)-Pyrrolidinemethanol | 4 | 7.95d(J=8Hz, 1H, aryl); 7.89d(J=2.1Hz, 1H, aryl); 7.77dd(J=8Hz/2.1Hz, 1H, aryl); 3.67m(2H, CH$_2$N); 3.62dd (J=10.5Hz/3.8Hz, 1H, CH$_2$OH); 3.39 dd(J=10.5Hz/2.5Hz, 1H, CH$_2$OH); 3.18m(1H, CH$_2$N); 2.71dddbr(J=11.8Hz/8Hz/8Hz, 1H, CH$_2$N); 2.57m (1H, CH$_2$N); 2.25m(1H, CH$_2$N); 2.24 m(1H, CH$_2$N); 1.95–1.66m(4H, CH$_2$); 1.80m(2H, CH$_2$); 1.58s(6H, CH$_3$); 1.51m(2H, CH$_2$); 1.39m(6H, CH$_2$) |
| 9 | 4-[3-[7-[(2S)-2-(Hydroxymethyl)-pyrrolidin-1-yl]heptyl]-4,4-dimethyl-5-oxo-2-thioxo-imidazolidin-1-yl]-2-(trifluoromethyl)-benzonitrile (2S)-Pyrrolidinemethanol | 4 | 7.95d(J=8Hz, 1H, aryl); 7.89d(J=2.1Hz, 1H, aryl); 7.77dd(J=8Hz/2.1Hz, 1H, aryl); 3.67m(2H, CH$_2$N); 3.62dd (J=10.5Hz/3.8Hz, 1H, CH$_2$OH); 3.39 dd(J=10.5Hz/2.5Hz, 1H, CH$_2$OH); 3.18m(1H, CH$_2$N); 2.71dddbr(J=11.8Hz/8Hz/8Hz, 1H, CH$_2$N); 2.57m (1H, CH$_2$N); 2.25m(1H, CH$_2$N); 2.24 m(1H, CH$_2$N); 1.95–1.66m(4H, CH$_2$); 1.80m(2H, CH$_2$); 1.58s(6H, CH$_3$); 1.51m(2H, CH$_2$); 1.39m(6H, CH$_2$) |
| 10 | 4-[3-[8-[(2R)-2-(Hydroxymethyl)-pyrrolidin-1-yl]octyl]-4,4-dimethyl-5-oxo-2-thioxoimidazolidin-1-yl]-2-(trifluoromethyl)-benzonitrile (2R)-Pyrrolidinemethanol | 1 | 7.95d(J=8Hz, 1H, aryl); 7.89d(J=2.1Hz, 1H, aryl); 7.78dd(J=8Hz/2.1Hz, 1H, aryl); 3.67m(2H, CH$_2$N); 3.63dd (J=10.5Hz/3.8Hz, 1H, CH$_2$OH); 3.39 dd(J=10.5Hz/2.5Hz, 1H, CH$_2$OH); 3.18m(1H, CH$_2$N); 2.71dddbr(J=11.8Hz/8Hz/8Hz, 1H, CH$_2$N); 2.58m (1H, CH$_2$N); 2.25m(2H, CH$_2$N); 1.96–1.67 m(4H, CH$_2$); 1.82m(2H, CH$_2$); 1.58s(6H, CH$_3$); 1.50m(2H, CH$_2$); 1.36m(8H, CH$_2$) |
| 11 | 4-[3-[8-[(2S)-2-(Hydroxymethyl)-pyrrolidin-1-yl]octyl]-4,4-dimethyl-5-oxo-2-thioxoimidazolidin-1-yl]-2-(trifluoromethyl)-benzonitrile (2S)-Pyrrolidinemethanol | 1 | 7.95d(J=8Hz, 1H, aryl); 7.89d(J=2.1Hz, 1H, aryl); 7.78dd(J=8Hz/2.1Hz, 1H, aryl); 3.67m(2H, CH$_2$N); 3.63dd (J=10.5Hz/3.8Hz, 1H, CH$_2$OH); 3.39 dd(J=10.5Hz/2.5Hz, 1H, CH$_2$OH); 3.18m(1H, CH$_2$N); 2.71dddbr(J=11.8Hz/8Hz/8Hz, 1H, CH$_2$N); 2.58m (1H, CH$_2$N); 2.25m(2H, CH$_2$N); 1.96–1.67 m(4H, CH$_2$); 1.82m(2H, CH$_2$); 1.58s(6H, CH$_3$); 1.50m(2H, CH$_2$); 1.36 m(8H, CH$_2$) |
| 12 | 4-[3-[9-[(2R)-2-(Hydroxymethyl)-pyrrolidin-1-yl]nonyl]-4,4-dimethyl-5-oxo-2-thioxoimidazolidin-1-yl]-2-(trifluoromethyl)-benzonitrile (2R)-Pyrrolidinemethanol | 5 | 7.95d(J=8Hz, 1H, aryl); 7.90d(J=2.1Hz, 1H, aryl); 7.77dd(J=8Hz/2.1Hz, 1H, aryl); 3.67m(2H, CH$_2$N); 3.62dd (J=10.5Hz/3.8Hz, 1H, CH$_2$OH); 3.38 dd(J=10.5Hz/2.5Hz, 1H, CH$_2$OH); 3.17m(1H, CH$_2$N); 2.70dddbr(J=11.8Hz/8.4Hz/8Hz, 1H, CH$_2$N); 2.56m (1H, CH$_2$N); 2.24m(1H, CH$_2$N); 2.21 m(1H, CH$_2$N); 1.92–1.67m(4H, CH$_2$); 1.82m(2H, CH$_2$); 1.58s(6H, CH$_3$); 1.48m(2H, CH$_2$); 1.31m(10H, CH$_2$) |
| 13 | 4-[3-[9-[(2S)-2-(Hydroxymethyl)-pyrrolidin-1-yl]nonyl]-4,4-dimethyl-5-oxo-2-thioxoimidazolidin-1-yl]-2-(trifluoromethyl)-benzonitrile (2S)-Pyrrolidinemethanol | 5 | 7.95d(J=8Hz, 1H, aryl); 7.90d(J=2.1Hz, 1H, aryl); 7.77dd(J=8Hz/2.1Hz, 1H, aryl); 3.67m(2H, CH$_2$N); 3.62dd (J=10.5Hz/3.8Hz, 1H, CH$_2$OH); 3.38 dd(J=10.5Hz/2.5Hz, 1H, CH$_2$OH); 3.17m(1H, CH$_2$N); 2.70dddbr(J=11.8Hz/8.4Hz/8Hz, 1H, CH$_2$N); 2.56m (1H, CH$_2$N); 2.24m(1H, CH$_2$N); 2.21 m(1H, CH$_2$N); 1.92–1.67m(4H, CH$_2$); 1.82m(2H, CH$_2$); 1.58s(6H, CH$_3$); 1.48m(2H, CH$_2$); 1.31m(10H, CH$_2$) |
| 14 | 4-[3-[6-[(2R)-2-(Methoxymethyl)-pyrrolidin-1-yl]hexyl]- | 3 | 7.95d(J=8Hz, 1H, aryl); 7.89d(J=2.1Hz, 1H, aryl); 7.77dd(J=8Hz/2.1Hz, 1H, aryl); 3.67m(2H, CH$_2$N); 3.42dd |

-continued

| Example | Product/ Reagent | Instructions analagous to | $^1$H-NMR(300 MHz, CDCl$_3$) δ [ppm] |
|---|---|---|---|
|  | 4,4-dimethyl-5-oxo-2-thioxoimidazolidin-1-yl]-2-(trifluoromethyl)-benzonitrile (2R)-2-(Methoxymethyl) pyrrolidine |  | (J=9.3Hz/5.1Hz, 1H, CH$_2$O); 3.35s (3H, CH$_3$O); 3.28dd(J=9.3Hz/5.9Hz, 1H, CH$_2$O); 3.16m(1H, CH$_2$N); 2.85 dddbr(J=11.8Hz/8.4Hz/8Hz, 1H, CH$_2$N); 2.56m(1H, CH$_2$N); 2.26dddbr (J=11.8Hz/7.6Hz/7.6Hz, 1H, CH$_2$N); 2.17m(1H, CH$_2$N); 1.92–1.67 m(4H, CH$_2$); 1.83m(2H, CH$_2$); 1.57s (6H, CH$_3$); 1.54m(2H, CH$_2$); 1.40m (4H, CH$_2$) |
| 15 | 4-[3-[6-[(2S)-2-(Methoxymethyl)-pyrrolidin-1-yl]hexyl]-4,4-dimethyl-5-oxo-2-thioxoimidazolidin-1-yl]-2-(trifluoromethyl)-benzonitrile (2S)-2-(Methoxymethyl) pyrrolidine | 3 | 7.95d(J=8Hz, 1H, aryl); 7.89d(J=2.1Hz, 1H, aryl); 7.77dd(J=8Hz/2.1Hz, 1H, aryl); 3.67m(2H, CH$_2$N); 3.42dd (J=9.3Hz/5.1Hz, 1H, CH$_2$O); 3.35s (3H, CH$_3$O); 3.28dd(J=9.3Hz/5.9Hz, 1H, CH$_2$O); 3.16m(1H, CH$_2$N); 2.85 dddbr(J=11.8Hz/8.4Hz/8Hz, 1H, CH$_2$N); 2.56m(1H, CH$_2$N); 2.26dddbr (J=11.8Hz/7.6Hz/7.6Hz, 1H, CH$_2$N); 2.17m(1H, CH$_2$N); 1.92–1.67 m(4H, CH$_2$); 1.83m(2H, CH$_2$); 1.57s (6H, CH$_3$); 1.54m(2H, CH$_2$); 1.40m (4H, CH$_2$) |
| 16 | 4-[3-[7-[(2R)-2-(Methoxymethyl)-pyrrolidin-1-yl]heptyl]-4,4-dimethyl-5-oxo-2-thioxoimidazolidin-1-yl]-2-(trifluoromethyl)-benzonitrile (2R)-2-(Methoxymethyl)-pyrrolidine | 4 | 7.95d(J=8Hz, 1H, aryl); 7.89d(J=2.1Hz, 1H, aryl); 7.77dd(J=8Hz/2.1Hz, 1H, aryl); 3.66m(2H, CH$_2$N); 3.42dd (J=9.3Hz/5.1Hz, 1H, CH$_2$O); 3.35s (3H, CH$_3$O); 3.27dd(J=9.3Hz/5.9Hz, 1H, CH$_2$O); 3.14m(1H, CH$_2$N); 2.83 dddbr(J=11.8Hz/8.4Hz/8Hz, 1H, CH$_2$N); 2.55m(1H, CH$_2$N); 2.24dddbr (J=11.8Hz/7.6Hz/7.6Hz, 1H, CH$_2$N); 2.16m(1H, CH$_2$N); 1.92–1.67 m(4H, CH$_2$); 1.83m(2H, CH$_2$); 1.58s (6H, CH$_3$); 1.51m(2H, CH$_2$); 1.38m (6H, CH$_2$) |
| 17 | 4-[3-[7-[(2S)-2-(Methoxymethyl)-pyrrolidin-1-yl]heptyl]-4,4-dimethyl-5-oxo-2-thioxoimidazolidin-1-yl]-2-(trifluoromethyl)-benzonitrile (2S)-2-(Methoxymethyl) pyrrolidine | 4 | 7.95d(J=8Hz, 1H, aryl); 7.89d(J=2.1Hz, 1H, aryl); 7.77dd(J=8Hz/2.1Hz, 1H, aryl); 3.66m(2H, CH$_2$N); 3.42dd (J=9.3Hz/5.1Hz, 1H, CH$_2$O); 3.35s (3H, CH$_3$O); 3.27dd(J=9.3Hz/5.9Hz, 1H, CH$_2$O); 3.14m(1H, CH$_2$N); 2.83 dddbr(J=11.8Hz/8.4Hz/8Hz, 1H, CH$_2$N); 2.55m(1H, CH$_2$N); 2.24dddbr (J=11.8Hz/7.6Hz/7.6Hz, 1H, CH$_2$N); 2.16m(1H, CH$_2$N); 1.92–1.67 m(4H, CH$_2$); 1.83m(2H, CH$_2$); 1.58s (6H, CH$_3$); 1.51m(2H, CH$_2$); 1.38m (6H, CH$_2$) |
| 18 | 4-[3-[8-[(2R)-2-(Methoxymethyl)-pyrrolidin-1-yl]octyl]-4,4-dimethyl-5-oxo-2-thioxoimidazolidin-1-yl]-2-(trifluoromethyl)-benzonitrile (2R)-2-(Methoxymethyl) pyrrolidine | 1 | 7.94d(J=8Hz, 1H, aryl); 7.89d(J=2.1Hz, 1H, aryl); 7.77dd(J=8Hz/2.1Hz, 1H, aryl); 3.66m(2H, CH$_2$N); 3.43dd (J=9.3Hz/5.1Hz, 1H, CH$_2$O); 3.35s (3H, CH$_3$O); 3.27dd(J=9.3Hz/5.9Hz, 1H, CH$_2$O); 3.15m(1H, CH$_2$N); 2.82 dddbr(J=11.8Hz/8.4Hz/8Hz, 1H, CH$_2$N); 2.56m(1H, CH$_2$N); 2.24dddbr (J=11.8Hz/7.6Hz/7.6Hz, 1H, CH$_2$N); 2.17m(1H, CH$_2$N); 1.92–1.67 m(4H, CH$_2$); 1.82m(2H, CH$_2$); 1.58s (6H, CH$_3$); 1.51m(2H, CH$_2$); 1.36m (8H, CH$_2$) |
| 19 | 4-[3-[8-[(2S)-2-(Methoxymethyl)-pyrrolidin-1-yl]octyl]-4,4-dimethyl-5-oxo-2-thioxoimidazolidin-1-yl]-2-(trifluoromethyl)-benzonitrile (2S)-2-(Methoxymethyl) pyrrolidine | 1 | 7.94d(J=8Hz, 1H, aryl); 7.89d(J=2.1Hz, 1H, aryl); 7.77dd(J=8Hz/2.1Hz, 1H, aryl); 3.66m(2H, CH$_2$N); 3.43dd (J=9.3Hz/5.1Hz, 1H, CH$_2$O); 3.35s (3H, CH$_3$O); 3.27dd(J=9.3Hz/5.9Hz, 1H, CH$_2$O); 3.15m(1H, CH$_2$N); 2.82 dddbr(J=11.8Hz/8.4Hz/8Hz, 1H, CH$_2$N); 2.56m(1H, CH$_2$N); 2.24dddbr (J=11.8Hz/7.6Hz/7.6Hz, 1H, CH$_2$N); 2.17m(1H, CH$_2$N); 1.92–1.67 m(4H, CH$_2$); 1.82m(2H, CH$_2$); 1.58s (6H, CH$_3$); 1.51m(2H, CH$_2$); 1.36m (8H, CH$_2$) |

-continued

| Example | Product/Reagent | Instructions analagous to | $^1$H-NMR(300 MHz, CDCl$_3$) δ [ppm] |
|---|---|---|---|
| 20 | 4-[3-[9-[(2R)-2-(Methoxymethyl)-pyrrolidin-1-yl]nonyl]-4,4-dimethyl-5-oxo-2-thioxoimidazolidin-1-yl]-2-(trifluoromethyl)-benzonitrile (2R)-2-(Methoxymethyl) pyrrolidine | 5 | 7.95d(J=8Hz, 1H, aryl); 7.89d(J=2.1Hz, 1H, aryl); 7.77dd(J=8Hz/2.1Hz, 1H, aryl); 3.66m(2H, CH$_2$N); 3.41dd (J=9.3Hz/5.1Hz, 1H, CH$_2$O); 3.35s (3H, CH$_3$O); 3.27dd(J=9.3Hz/5.9Hz, 1H, CH$_2$O); 3.13m(1H, CH$_2$N); 2.80 dddbr(J=11.8Hz/8.4Hz/8Hz, 1H, CH$_2$N); 2.53m(1H, CH$_2$N); 2.22dddbr (J=11.8Hz/7.6Hz/7.6Hz, 1H, CH$_2$N); 2.15m(1H, CH$_2$N); 1.92–1.67 m(4H, CH$_2$); 1.83m(2H, CH$_2$); 1.58s (6H, CH$_3$); 1.49m(2H, CH$_2$); 1.31m (10H, CH$_2$) |
| 21 | 4-[3-[9-[(2S)-2-(Methoxymethyl)-pyrrolidin-1-yl]nonyl]-4,4-dimethyl-5-oxo-2-thioxoimidazolidin-1-yl]-2-(trifluoromethyl)-benzonitrile (2S)-2-(Methoxymethyl) pyrrolidine | 5 | 7.95d(J=8Hz, 1H, aryl); 7.89d(J=2.1Hz, 1H, aryl); 7.77dd(J=8Hz/2.1Hz, 1H, aryl); 3.66m(2H, CH$_2$N); 3.41dd (J=9.3Hz/5.1Hz, 1H, CH$_2$O); 3.35s (3H, CH$_3$O); 3.27dd(J=9.3Hz/5.9Hz, 1H, CH$_2$O); 3.13m(1H, CH$_2$N); 2.80 dddbr(J=11.8Hz/8.4Hz/8Hz, 1H, CH$_2$N); 2.53m(1H, CH$_2$N); 2.22dddbr (J=11.8Hz/7.6Hz/7.6Hz, 1H, CH$_2$N); 2.15m(1H, CH$_2$N); 1.92–1.67 m(4H, CH$_2$); 1.83m(2H, CH$_2$); 1.58s (6H, CH$_3$); 1.49m(2H, CH$_2$); 1.31m (10H, CH$_2$) |
| 22 | 4-[3-[6-(3-Hydroxy-8-azabicyclo[3.2.1]oct-8-yl)hexyl]-4,4-dimethyl-5-oxo-2-thioxoimidazolidin-1-yl]-2-(trifluoromethyl)-benzonitrile 8-Azabicyclo[3.2.1]-octan-3-ol | 3 | 7.95d(J=8Hz, 1H, aryl); 7.90d(J=2.1Hz, 1H, aryl); 7.79dd(J=8Hz/2.1Hz, 1H, aryl); 4.04m(1H, CHOH); 3.69m (2H, CH$_2$N); 3.19m(2H, CHN); 2.35m (2H, CH$_2$N); 2.05m(4H, CH$_2$); 1.91m (2H, CH$_2$); 1.86m(2H, CH$_2$); 1.62m (2H, CH$_2$); 1.58s(6H, CH$_3$); 1.53m (2H, CH$_2$); 1.40m(4H, CH$_2$) |
| 23 | 4-[3-[7-(3-Hydroxy-8-azabicyclo[3.2.1]oct-8-yl)heptyl]-4,4-dimethyl-5-oxo-2-thioxoimidazolidin-1-yl]-2-(trifluoromethyl)-benzonitrile 8-Azabicyclo[3.2.1]-octan-3-ol | 4 | 7.95d(J=8Hz, 1H, aryl); 7.89d(J=2.1Hz, 1H, aryl); 7.77dd(J=8Hz/2.1Hz, 1H, aryl); 4.05m(1H, CHOH); 3.66m (2H, CH$_2$N); 3.19m(2H, CHN); 2.33m (2H, CH$_2$N); 2.07m(4H, CH$_2$); 1.92m (2H, CH$_2$); 1.82m(2H, CH$_2$); 1.62m (2H, CH$_2$); 1.58s(6H, CH$_3$); 1.49m (2H, CH$_2$); 1.38m(6H, CH$_2$) |
| 24 | 4-[3-[8-(3-Hydroxy-8-azabicyclo[3.2.1]oct-8-yl)octyl]-4,4-dimethyl-5-oxo-2-thioxoimidazolidin-1-yl]-2-(trifluoromethyl)-benzonitrile 8-Azabicyclo[3.2.1]-octan-3-ol | 1 | 7.95d(J=8Hz, 1H, aryl); 7.89d(J=2.1Hz, 1H, aryl); 7.78dd(J=8Hz/2.1Hz, 1H, aryl); 4.05m(1H, CHOH); 3.66m (2H, CH$_2$N); 3.19m(2H, CHN); 2.33m (2H, CH$_2$N); 2.07m(4H, CH$_2$); 1.92m (2H, CH$_2$); 1.81m(2H, CH$_2$); 1.62m (2H, CH$_2$); 1.59s(6H, CH$_3$); 1.48m (2H, CH$_2$); 1.38m(8H, CH$_2$) |
| 25 | 4-[3-[9-(3-Hydroxy-8-azabicyclo[3.2.1]oct-8-yl)nonyl]-4,4-dimethyl-5-oxo-2-thioxoimidazolidin-1-yl]-2-(trifluoromethyl)-benzonitrile 8-Azabicyclo[3.2.1]-octan-3-ol | 5 | 7.95d(J=8Hz, 1H, aryl); 7.89d(J=2.1Hz, 1H, aryl); 7.77dd(J=8Hz/2.1Hz, 1H, aryl); 4.04m(1H, CHOH); 3.66m (2H, CH$_2$N); 3.19m(2H, CHN); 2.33m (2H, CH$_2$N); 2.08m(4H, CH$_2$); 1.91m (2H, CH$_2$); 1.82m(2H, CH$_2$); 1.62m (2H, CH$_2$); 1.58s(6H, CH$_3$); 1.48m (2H, CH$_2$); 1.31m(10H, CH$_2$) |
| 26 | 4-[3-[6-[(R)-3-Hydroxypyrrolidin-1-yl]hexyl]-4,4-dimethyl-5-oxo-2-thioxoimidazolidin-1-yl]-2-(trifluoromethyl)-benzonitrile (R)-Pyrrolidin-3-ol | 3 | 7.95d(J=8Hz, 1H, aryl); 7.89d(J=2.1Hz, 1H, aryl); 7.77dd(J=8Hz/2.1Hz, 1H, aryl); 4.34m(1H, CHOH); 3.67m (2H, CH$_2$N); 2.89m(1H, CH$_2$N); 2.69 m(1H, CH$_2$N); 2.50m(1H, CH$_2$N); 2.46m(2H, CH$_2$N); 2.28m(1H, CH$_2$N); 2.20m(1H, CH$_2$); 1.83m(2H, CH$_2$); 1.74m(1H, CH$_2$); 1.57s(6H, CH$_3$); 1.56m(2H, CH$_2$); 1.41m(4H, CH$_2$) |
| 27 | 4-[3-[7-[(R)-3-Hydroxypyrrolidin-1-yl]heptyl]-4,4-dimethyl-5-oxo-2-thioxoimidazolidin- | 4 | 7.95d(J=8Hz, 1H, aryl); 7.89d(J=2.1Hz, 1H, aryl); 7.77dd(J=8Hz/2.1Hz, 1H, aryl); 4.34m(1H, CHOH); 3.66m (2H, CH$_2$N); 2.89m(1H, CH$_2$N); 2.69 |

-continued

| Example | Product/ Reagent | Instructions analagous to | $^1$H-NMR(300 MHz, CDCl$_3$) δ [ppm] |
|---|---|---|---|
| | 1-yl]-2-(trifluoromethyl)-benzonitrile (R)-Pyrrolidin-3-ol | | m(1H, CH$_2$N); 2.52m(1H, CH$_2$N); 2.45m(2H, CH$_2$N); 2.30m(1H, CH$_2$N); 2.17m(1H, CH$_2$); 1.83m(2H, CH$_2$); 1.74m(1H, CH$_2$); 1.58s(6H, CH$_3$); 1.52m(2H, CH$_2$); 1.39m(6H, CH$_2$) |
| 28 | 4-[3-[8-[(R)-3-Hydroxypyrrolidin-1-yl]octyl]-4,4-dimethyl-5-oxo-2-thioxoimidazolidin-1-yl]-2-(trifluoromethyl)-benzonitrile (R)-Pyrrolidin-3-ol | 1 | 7.95d(J=8Hz, 1H, aryl); 7.89d(J=2.1Hz, 1H, aryl); 7.77dd(J=8Hz/2.1Hz, 1H, aryl); 4.34m(1H, CHOH); 3.66m (2H, CH$_2$N); 2.89m(1H, CH$_2$N); 2.70 m(1H, CH$_2$N); 2.53m(1H, CH$_2$N); 2.45m(2H, CH$_2$N); 2.30m(1H, CH$_2$N); 2.19m(1H, CH$_2$); 1.82m(2H, CH$_2$); 1.75m(1H, CH$_2$); 1.58s(6H, CH$_3$); 1.51m(2H, CH$_2$); 1.35m(8H, CH$_2$) |
| 29 | 4-[3-[9-[(R)-3-Hydroxypyrrolidin-1-yl]nonyl]-4,4-dimethyl-5-oxo-2-thioxoimidazolidin-1-yl]-2-(trifluoromethyl)-benzonitrile (R)-Pyrrolidin-3-ol | 5 | 7.95d(J=8Hz, 1H, aryl); 7.89d(J=2.1Hz, 1H, aryl); 7.77dd(J=8Hz/2.1Hz, 1H, aryl); 4.32m(1H, CHOH); 3.66m (2H, CH$_2$N); 2.87m(1H, CH$_2$N); 2.66 m(1H, CH$_2$N); 2.48m(1H, CH$_2$N); 2.41m(2H, CH$_2$N); 2.25m(1H, CH$_2$N); 2.17m(1H, CH$_2$); 1.82m(2H, CH$_2$); 1.72m(1H, CH$_2$); 1.58s(6H, CH$_3$); 1.49m(2H, CH$_2$); 1.31m(10H, CH$_2$) |
| 30 | 4-[3-[6-[(S)-3-Hydroxypyrrolidin-1-yl]hexyl]-4,4-dimethyl-5-oxo-2-thioxoimidazolidin-1-yl]-2-(trifluoromethyl)-benzonitrile (S)-Pyrrolidin-3-ol | 3 | 7.95d(J=8Hz, 1H, aryl); 7.89d(J=2.1Hz, 1H, aryl); 7.77dd(J=8Hz/2.1Hz, 1H, aryl); 4.37m(1H, CHOH); 3.67m (2H, CH$_2$N); 2.94m(1H, CH$_2$N); 2.75 m(1H, CH$_2$N); 2.59m(1H, CH$_2$N); 2.51m(2H, CH$_2$N); 2.37m(1H, CH$_2$N); 2.21m(1H, CH$_2$); 1.83m(2H, CH$_2$); 1.81m(1H, CH$_2$); 1.58s(6H, CH$_3$); 1.57m(2H, CH$_2$); 1.42m(4H, CH$_2$) |
| 31 | 4-[3-[7-[(S)-3-Hydroxypyrrolidin-1-yl]heptyl]-4,4-dimethyl-5-oxo-2-thioxoimidazolidin-1-yl]-2-(trifluoromethyl)-benzonitrile (S)-Pyrrolidin-3-ol | 4 | 7.95d(J=8Hz, 1H, aryl); 7.89d(J=2.1Hz, 1H, aryl); 7.77dd(J=8Hz/2.1Hz, 1H, aryl); 4.37m(1H, CHOH); 3.66m (2H, CH$_2$N); 2.95m(1H, CH$_2$N); 2.75 m(1H, CH$_2$N); 2.61m(1H, CH$_2$N); 2.52m(2H, CH$_2$N); 2.40m(1H, CH$_2$N); 2.21m(1H, CH$_2$); 1.83m(2H, CH$_2$); 1.81m(1H, CH$_2$); 1.58s(6H, CH$_3$); 1.56m(2H, CH$_2$); 1.39m(6H, CH$_2$) |
| 32 | 4-[3-[8-[(S)-3-Hydroxypyrrolidin-1-yl]octyl]-4,4-dimethyl-5-oxo-2-thioxoimidazolidin-1-yl]-2-(trifluoromethyl)-benzonitrile (S)-Pyrrolidin-3-ol | 1 | 7.95d(J=8Hz, 1H, aryl); 7.89d(J=2.1Hz, 1H, aryl); 7.77dd(J=8Hz/2.1Hz, 1H, aryl); 4.34m(1H, CHOH); 3.67m (2H, CH$_2$N); 2.89m(1H, CH$_2$N); 2.70 m(1H, CH$_2$N); 2.53m(1H, CH$_2$N); 2.45m(2H, CH$_2$N); 2.30m(1H, CH$_2$N); 2.19m(1H, CH$_2$); 1.82m(2H, CH$_2$); 1.75m(1H, CH$_2$); 1.58s(6H, CH$_3$); 1.51m(2H, CH$_2$); 1.36m(8H, CH$_2$) |
| 33 | 4-[3-[9-[(S)-3-Hydroxypyrrolidin-1-yl]nonyl]-4,4-dimethyl-5-oxo-2-thioxoimidazolidin-1-yl]-2-(trifluoromethyl)-benzonitrile (S)-Pyrrolidin-3-ol | 5 | 7.95d(J=8Hz, 1H, aryl); 7.89d(J=2.1Hz, 1H, aryl); 7.77dd(J=8Hz/2.1Hz, 1H, aryl); 4.33m(1H, CHOH); 3.66m (2H, CH$_2$N); 2.87m(1H, CH$_2$N); 2.67 m(1H, CH$_2$N); 2.49m(1H, CH$_2$N); 2.42m(2H, CH$_2$N); 2.26m(1H, CH$_2$N); 2.17m(1H, CH$_2$); 1.82m(2H, CH$_2$); 1.72m(1H, CH$_2$); 1.58s(6H, CH$_3$); 1.49m(2H, CH$_2$); 1.31m(10H, CH$_2$) |
| 34 | 4-[4,4-Dimethyl-3-[6-(2-methylpyrrolidin-1-yl)hexyl]-5-oxo-2-thioxoimidazolidin-1-yl]-2-(trifluoromethyl)-benzonitrile 2-Methylpyrrolidine | 3 | 7.95d(J=8Hz, 1H, aryl); 7.89d(J=2.1Hz, 1H, aryl); 7.77dd(J=8Hz/2.1Hz, 1H, aryl); 3.67m(2H, CH$_2$N); 3.17m (1H, CH$_2$N); 2.79m(1H, CH$_2$N); 2.27 m(1H, CHN); 2.06m(1H, CH$_2$N); 2.03 m(1H, CH$_2$N); 2.00–1.35m(4H, CH$_2$); 1.83m(2H, CH$_2$); 1.57s(6H, CH$_3$); 1.57m(2H, CH$_2$); 1.41m(4H, CH$_2$); 1.10d(J=6Hz, 3H, CH$_3$) |

| Example | Product/Reagent | Instructions analagous to | $^1$H-NMR(300 MHz, CDCl$_3$) δ [ppm] |
|---|---|---|---|
| 35 | 4-[4,4-Dimethyl-3-[7-(2-methylpyrrolidin-1-yl)heptyl]-5-oxo-2-thioxoimidazolidin-1-yl]-2-(trifluoromethyl)-benzonitrile<br>2-Methylpyrrolidine | 4 | 7.94d(J=8Hz, 1H, aryl); 7.89d(J=2.1Hz, 1H, aryl); 7.77dd(J=8Hz/2.1Hz, 1H, aryl); 3.66m(2H, CH$_2$N); 3.16m (1H, CH$_2$N); 2.78m(1H, CH$_2$N); 2.24 m(1H, CHN); 2.06m(1H, CH$_2$N); 2.02 m(1H, CH$_2$N); 2.00–1.35m(4H, CH$_2$); 1.82m(2H, CH$_2$); 1.57s(6H, CH$_3$); 1.52m(2H, CH$_2$); 1.38m(6H, CH$_2$); 1.10d(J=6Hz, 3H, CH$_3$) |
| 36 | 4-[4,4-Dimethyl-3-[8-(2-methylpyrrolidin-1-yl)octyl]-5-oxo-2-thioxoimidazolidin-1-yl]-2-(trifluoromethyl)-benzonitrile<br>2-Methylpyrrolidine | 1 | 7.94d(J=8Hz, 1H, aryl); 7.89d(J=2.1Hz, 1H, aryl); 7.77dd(J=8Hz/2.1Hz, 1H, aryl); 3.66m(2H, CH$_2$N); 3.16m (1H, CH$_2$N); 2.77m(1H, CH$_2$N); 2.25 m(1H, CHN); 2.05m(1H, CH$_2$N); 2.03 m(1H, CH$_2$N); 2.00–1.35m(4H, CH$_2$); 1.82m(2H, CH$_2$); 1.58s(6H, CH$_3$); 1.51m(2H, CH$_2$); 1.35m(8H, CH$_2$); 1.10d(J=6Hz, 3H, CH$_3$) |
| 37 | 4-[3-[8-[(2R,5S)-rel-2,5-Dimethylpyrrolidin-1-yl]octyl]-4,4-dimethyl-5-oxo-2-thioxoimidazolidin-1-yl]-2-(trifluoromethyl)-benzonitrile<br>(2R,5S)-rel-2,5-Dimethylpyrrolidine | 1 | 7.95d(J=8Hz, 1H, aryl); 7.89d(J=2.1Hz, 1H, aryl); 7.78dd(J=8Hz/2.1Hz, 1H, aryl); 3.67m(2H, CH$_2$N); 2.57m (2H, CHN); 2.55m(2H, CH$_2$N); 1.80m (2H, CH$_2$); 1.82m(2H, CH$_2$); 1.58s (6H, CH$_3$); 1.46m(2H, CH$_2$); 1.30m (2H, CH$_2$); 1.35m(8H, CH$_2$); 1.11d (J=6Hz, 6H, CH$_3$) |
| 38 | 4-[3-[6-[(2S)-2-(1-Hydroxy-1-methyl-ethyl)pyrrolidin-1-yl]hexyl]-4,4-dimethyl-5-oxo-2-thioxoimidazolidin-1-yl]-2-(trifluoromethyl)-benzonitrile<br>(2S)-α,α-Dimethylpyrrolidinemethanol, produced from L-prolinemethyl ester according to K. Nakayama, W. J. Thompson, J. Am. Chem. Soc. 112, 6936–6942 (1990) | 3 | 1.12(s, 3H); 1.21(s, b, 3H); 1.30–1.48 (b, 4H); 1.58(s, 6H); 1.49–1.95(b, 9H); 2.33–2.72(b, 3H); 2.73–2.96(b, 1H); 2.99–3.28(b, 1H); 3.65–3.70(m, 2H); 7.77(dd, J=2.11Hz, 8.43Hz; 1H); 7.89 (d, J=1.68Hz; 1H); 7.95(d, J=8.43Hz; 1H) |
| 39 | 4-[3-[7-[(2S)-2-(1-Hydroxy-1-methylethyl)pyrrolidin-1-yl]heptyl]-4,4-dimethyl-5-oxo-2-thioxoimidazolidin-1-yl]-2-(trifluoromethyl)-benzonitrile<br>(2S)-α,α-Dimethylpyrrolidinemethanol | 4 | 1.11(s, 3H); 1.20(s, b, 3H); 1.30–1.47 (b, 6H); 1.58(s, 6H); 1.50–1.92(b, 9H); 2.35–2.68(b, 3H); 2.70–2.91(b, 1H); 3.00–3.22(b, 1H); 3.64–3.69(m, 2H); 7.77(dd, J=1.90Hz, 8.26Hz; 1H); 7.89 (d, J=2.10Hz; 1H); 7.95(d, J=8.43Hz; 1H) |
| 40 | 4-[3-[8-[(2S)-2-(1-Hydroxy-1-methylethyl)pyrrolidin-1-yl]octyl]-4,4-dimethyl-5-oxo-2-thioxoimidazolidin-1-yl]-2-(trifluoromethyl)-benzonitrile<br>(2S)-α,α-Dimethylpyrrolidinemethanol | 1 | 1.12(s, 3H); 1.22(s, b, 3H); 1.27–1.44 (b, 8H); 1.58(s, 6H); 1.50–1.92(b, 10H); 2.36–2.70(b, 2H); 2.71–2.95(b, 1H); 3.00–3.23(b, 1H); 3.64–3.70(m, 2H); 7.77(dd, J=2.11Hz, 8.43Hz; 1H); 7.89 (d, J=2.11Hz; 1H); 7.95(d, J=8.43Hz; 1H) |
| 41 | 4-[3-[9-[(2S)-2-(1-Hydroxy-1-methylethyl)pyrrolidin-1-yl]nonyl]-4,4-dimethyl-5-oxo-2-thioxoimidazolidin-1-yl]-2-(trifluoromethyl)-benzonitrile<br>(2S)-α,α-Dimethylpyrrolidinemethanol | 5 | 1.11(s, 3H); 1.18(s, b, 3H); 1.24–1.44 (b, 10H); 1.45–1.55(b, 2H); 1.58(s, 6H); 1.63–1.90(b, 7H); 2.30–3.20(b, 5H); 3.64–3.69(m, 2H); 7.78(dd, J=2.10Hz, 8.43Hz; 1H); 7.90(d, J=2.53Hz; 1H); 7.95(d, J=8.01Hz; 1H) |
| 42 | 4-[3-[6-[(2R)-2-(1-Hydroxy-1-methylethyl)pyrrolidin- | 3 | 1.10(s, 3H); 1.18(s, b, 3H); 1.29–1.47 (b, 4H); 1.58(s, 6H); 1.48–1.91(b, 9H); 2.30–2.65(b, 3H); 2.68–2.92(b, 1H); |

| Example | Product/Reagent | Instructions analagous to | $^1$H-NMR(300 MHz, CDCl$_3$) δ [ppm] |
|---|---|---|---|
| | 1-yl]hexyl]-4,4-dimethyl-5-oxo-2-thioxoimidazolidin-1-yl]-2-(trifluoromethyl)-benzonitrile (2R)-α,α-Dimethylpyrrolidinemethanol, produced from D-prolinemethyl ester according to K. Nakayama, W. J. Thompson, J. Am. Chem. Soc. 112, 6936–6942 (1990) | | 2.95–3.18(b, 1H); 3.64–3.70(m, 2H); 7.77(dd, J=1.90Hz, 8.01Hz; 1H); 7.89 (d, J=1.68Hz; 1H); 7.95(d, J=8.43Hz; 1H) |
| 43 | 4-[3-[7-[(2R)-2-(1-Hydroxy-1-methylethyl)pyrrolidin-1-yl]heptyl]-4,4-dimethyl-5-oxo-2-thioxoimidazolidin-1-yl]-2-(trifluoromethyl)-benzonitrile (2R)-α,α-Dimethylpyrrolidinemethanol | 4 | 1.09(s, 3H); 1.17(s, b, 3H); 1.29–1.44 (b, 6H); 1.58(s, 6H); 1.46–1.90(b, 9H); 2.33–2.64(b, 3H); 2.68–2.86(b, 1H); 3.97–3.15(b, 1H); 3.64–3.69(m, 2H); 7.77(dd, J=2.11Hz, 8.01Hz; 1H); 7.89 (d, J=2.10Hz; 1H); 7.95(d, J=8.01Hz; 1H) |
| 44 | 4-[3-[8-[(2R)-2-(1-Hydroxy-1-methyl-ethyl)pyrrolidin-1-yl]octyl]-4,4-dimethyl-5-oxo-2-thioxoimidazolidin-1-yl]-2-(trifluoromethyl)-benzonitrile (2R)-α,α-Dimethylpyrrolidinemethanol | 1 | 1.11(s, 3H); 1.18(s, b, 3H); 1.23–1.44 (b, 8H); 1.58(s, 6H); 1.45–1.90(b, 9H); 2.30–3.15(b, 5H); 3.64–3.69(m, 2H); 7.78(dd, J=2.10Hz, 8.43Hz; 1H); 7.90 (d, J=2.11Hz; 1H); 7.95(d, J=8.43Hz; 1H) |
| 45 | 4-[3-[6-[(2S)-2-(1-Hydroxy-1-ethyl-propyl)pyrrolidin-1-yl]hexyl]-4,4-dimethyl-5-oxo-2-thioxoimidazolidin-1-yl]-2-(trifluoromethyl)-benzonitrile (2S)-α,α-Diethylpyrrolidinemethanol, produced from L-proline methyl ester according to K. Nakayama, W. J. Thompson, J. Am. Chem. Soc. 112, 6936–6942(1990) | 3 | 0.83(t, J=8.22Hz; 6H); 1.25–1.46(b, 6H); 1.59(s, 6H); 1.47–1.94(b, 11H); 2.36–2.56(b, 2H); 2.58–2.77(b, 2H); 2.87–3.03(b, 1H); 3.64–3.70(m, 2H); 7.77(dd, J=2.11Hz, 8.01Hz; 1H); 7.90 (d, J=2.11Hz; 1H); 7.95(d, J=8.00Hz; 1H) |
| 46 | 4-[3-[7-[(2S)-2-(1-Hydroxy-1-ethylpropyl)-pyrrolidin-1-yl]heptyl]-4,4-dimethyl-5-oxo-2-thioxoimidazolidin-1-yl]-2-(trifluoromethyl)-benzonitrile (2S)-α,α-Diethyl-pyrrolidinemethanol | 4 | 0.80–0.91(m, 6H); 1.22–1.47(b, 8H); 1.46–1.95(b, 11H); 1.58(s, 6H); 2.30–3.30 (b, 5H); 3.64–3.70(m, 2H); 7.77 (dd, J=2.11Hz, 8.01Hz; 1H); 7.89(d, J=1.68Hz; 1H); 7.95(d, J=8.01Hz; 1H) |
| 47 | 4-[3-[8-[(2S)-2-(1-Hydroxy-1-ethylpropyl)-pyrrolidin-1-yl]octyl]-4,4-dimethyl-5-oxo-2-thioxoimidazolidin-1-yl]-2-(trifluoromethyl)-benzonitrile (2S)-α,α-Diethylpyrrolidine-methanol | 1 | 0.84(t, J=7.80Hz; 6H); 1.20–1.43(b, 10H); 1.44–1.62(b, 4H); 1.59(s, 6H); 1.62–1.90(b, 7H); 2.35–2.56(b, 2H); 2.57–2.76(b, 2H); 2.85–3.04(b, 1H); 3.64–3.70(m, 2H); 7.78(dd, J=2.32Hz, 8.43Hz; 1H); 7.90(d, J=1.68Hz; 1H); 7.95(d, J=8.43Hz; 1H) |
| 48 | (S)-1-[7-[3-[4-Cyano-3-(trifluoromethyl) phenyl]-5,5-dimethyl-4-oxo-2-thioxoimidazolidin-1-yl]heptyl]pyrrolidine-2-carboxylic acidmethyl ester | 4 | 7.93d(J=8Hz, 1H, aryl); 7.88d(J=2.1Hz, 1H, aryl); 7.77dd(J=8Hz/2.1Hz, 1H, aryl); 3.70s(3H, OCH$_3$); 3.65m (2H, CH$_2$N); 3.17m(1H, CH$_2$N); 3.11 dd(J=9Hz/6Hz, 1H, CHN); 2.64m (1H, CH$_2$N); 2.33m(1H, CH$_2$N); 2.31 m(1H, CH$_2$N); 2.09m(1H, CH$_2$); 1.90 m(2H, CH$_2$); 1.82m(2H, CH$_2$); 1.80m |

-continued

| Example | Product/Reagent | Instructions analagous to | $^1$H-NMR(300 MHz, CDCl$_3$) δ [ppm] |
|---|---|---|---|
| | L-Prolinemethyl ester, Hydrochloride | | (1H, CH$_2$); 1.56s(6H, CH$_3$); 1.49m (2H, CH$_2$); 1.35m(6H, CH$_2$) |
| 49 | (S)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide L-Prolinamide | 3 | 7.95d(J=8Hz, 1H, aryl); 7.89d(J=2.1Hz 1H, aryl); 7.77dd(J=8Hz/2.1Hz, 1H, aryl); 7.22m(1H, CONH$_2$); 5.61m (1H, CONH$_2$); 3.66m(2H, CH$_2$N); 3.18 m(1H); 2.99m(1H); 2.64m(1H); 2.44 m(1H); 2.28m(1H); 2.17m(1H); 1.83 m(2H, CH$_2$); 1.80m(3H, CH$_2$); 1.58s (6H, CH$_3$); 1.51m(2H, CH$_2$); 1.40m (4H, CH$_2$) |
| 50 | (S)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide L-Prolinamide | 4 | 7.95d(J=8Hz, 1H, aryl); 7.89d(J=2.1Hz 1H, aryl); 7.77dd(J=8Hz/2.1Hz, 1H, aryl); 7.26m(1H, CONH$_2$); 5.39m (1H, CONH$_2$); 3.66m(2H, CH$_2$N); 3.18 m(1H); 3.00m(1H); 2.63m(1H); 2.45 m(1H); 2.30m(1H); 2.18m(1H); 1.89 m(1H, CH$_2$); 1.81m(2H, CH$_2$); 1.80m (2H, CH$_2$); 1.58s(6H, CH$_3$); 1.52m (2H, CH$_2$); 1.38m(6H, CH$_2$) |
| 51 | (S)-1-[8-[3-[4-Cyano-3-(trifluoromethyl)phenyl]-5,5-dimethyl-4-oxo-2-thioxoimidazolidin-1-yl]octyl]pyrrolidine-4-carboxamide L-Prolinamide | 1 | 7.95d(J=8Hz, 1H, aryl); 7.89d(J=2.1Hz 1H, aryl); 7.77dd(J=8Hz/2.1Hz, 1H, aryl); 7.27m(1H, CONH$_2$); 5.46m (1H, CONH$_2$); 3.66m(2H, CH$_2$N); 3.19 m(1H); 3.00m(1H); 2.63m(1H); 2.44 m(1H); 2.30m(1H); 2.18m(1H); 1.90 m(1H, CH$_2$); 1.81m(3H, CH$_2$); 1.66m (1H, CH$_2$); 1.58s(6H, CH$_3$); 1.49m (2H, CH$_2$); 1.35m(8H, CH$_2$) |
| 52 | (S)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide D-Prolinamide | 1 | 7.95d(J=8Hz, 1H, aryl); 7.89d(J=2.1Hz, 1H, aryl); 7.77dd(J=8Hz/2.1Hz, 1H, aryl); 7.77m(1H, CONH$_2$); 5.57m (1H, CONH$_2$); 3.66m(2H, CH$_2$N); 3.18 m(1H); 2.99m(1H); 2.64m(1H); 2.44 m(1H); 2.28m(1H); 2.17m(1H); 1.83 m(2H, CH$_2$); 1.80m(3H, CH$_2$); 1.58s (6H, CH$_3$); 1.51m(2H, CH$_2$); 1.40m (4H, CH$_2$) |
| 53 | (R)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide D-Prolinamide | 4 | 7.95d(J=8Hz, 1H, aryl); 7.89d(J=2.1Hz, 1H, aryl); 7.77dd(J=8Hz/2.1Hz, 1H, aryl); 7.26m(1H, CONH$_2$); 5.36m (1H, CONH$_2$); 3.66m(2H, CH$_2$N); 3.18 m(1H); 3.00m(1H); 2.63m(1H); 2.45 m(1H); 2.30m(1H); 2.18m(1H); 1.89 m(1H, CH$_2$); 1.81m(2H, CH$_2$); 1.80m (2H, CH$_2$); 1.58s(6H, CH$_3$); 1.52m (2H, CH$_2$); 1.38m(6H, CH$_2$) |
| 54 | (R)-1-[8-[3-[4-Cyano-3-(trifluoromethyl)phenyl]-5,5-dimethyl-4-oxo-2-thioxoimidazolidin-1-yl]octyl]pyrrolidine-4-carboxamide D-Prolinamide | 1 | 7.95d(J=8Hz, 1H, aryl); 7.89d(J=2.1Hz, 1H, aryl); 7.77dd(J=8Hz/2.1Hz, 1H, aryl); 7.24m(1H, CONH$_2$); 5.53m (1H, CONH$_2$); 3.66m(2H, CH$_2$N); 3.19 m(1H); 3.00m(1H); 2.63m(1H); 2.44 m(1H); 2.30m(1H); 2.18m(1H); 1.90 m(1H, CH$_2$); 1.81m(3H, CH$_2$); 1.66m (1H, CH$_2$); 1.58s(6H, CH$_3$); 1.49m (2H, CH$_2$); 1.35m(8H, CH$_2$) |
| 55 | 4-[3-[6-[(2S)-4,4-Dimethyl-5-oxo-2-(pyrrolidin-1-ylmethyl)-pyrrolidin-1-yl]hexyl]-2-thioxoimidazolidin-1-yl]-2-(trifluoromethyl)benzonitrile (2S)-2-(Pyrrolidin-1-ylmethyl)pyrrolidine, produced from L-proline according to M. Amedjkouh, P. Ahlberg, Tetrahedron: Asymmetry 13, 2229–2234(2002) | 3 | 1.34–1.49(b, 6H); 1.58(s, 6H); 1.65–189 (b, 8H); 1.90–2.09(b, 2H); 2.10–2.37 (b, 2H); 2.38–2.78(b, 7H); 2.84–3.01 (b, 1H); 3.15–3.26(b, 1H); 3.64–3.70 (m, 2H); 7.77(dd, J=2.11Hz, 8.43Hz; 1H); 7.89(d, J=1.68Hz; 1H); 7.95 (d, J=8.01Hz; 1H) |
| 56 | 4-[3-[7-[(2S)-4,4-Dimethyl-5-oxo-2-(pyrrolidin-1-ylmethyl)-pyrrolidin-1-yl]heptyl]-2-thioxoimidazolidin-1- | 4 | 1.28–1.44(b, 6H); 1.44–1.88(b, 10H); 1.58(s, 6H); 1.89–2.07(b, 2H); 2.08–2.25 (b, 2H); 2.31–2.70(b, 7H); 2.81–2.93 (b, 1H); 3.11–3.21(b, 1H); 3.64–3.69 (m, 2H); 7.77(dd, J=2.11Hz, 8.43Hz; |

-continued

| Example | Product/ Reagent | Instructions analagous to | $^1$H-NMR(300 MHz, CDCl$_3$) δ [ppm] |
|---|---|---|---|
| | yl]-2-(trifluoromethyl) benzonitrile (2S)-2-(Pyrrolidin-1-ylmethyl)pyrrolidine | | 1H); 7.89(d, J=1.68Hz; 1H); 7.95 (d, J=8.43Hz; 1H) |
| 57 | 4-[3-[8-[(2S)-4,4-Dimethyl-5-oxo-2-(pyrrolidin-1-ylmethyl)-pyrrolidin-1-yl]octyl]-2-thioxoimidazolidin-1-yl]-2-(trifluoromethyl) benzonitrile (2S)-2-(Pyrrolidin-1-ylmethyl)pyrrolidine | 1 | 1.22–1.43(b, 8H); 1.48–1.60(b, 2H); 1.58(s, 6H); 1.65–1.87(b, 8H); 1.92–2.08 (b, 2H); 2.09–2.29(b, 2H); 2.33–2.62 (b, 6H); 2.62–2.76(b, 1H); 2.80–2.97 (b, 1H); 3.11–3.25(b, 1H); 3.64–3.69 (m, 2H); 7.77(dd, J=1.69Hz, 8.01Hz; 1H); 7.89(d, J=1.26Hz; 1H); 7.95 (d, J=8.43Hz; 1H) |

EXAMPLE 58

(S)-1-[7-[3-[4-Cyano-3-(trifluoromethyl)phenyl]-5,5-dimethyl-4-oxo-2-thioxoimidazolidin-1-yl]heptyl]pyrrolidine-2-carboxylic acid hydrochloride 20 mg of the compound that is produced under 48 is stirred with a spatula tip full of potassium carbonate in 1 ml of methanol overnight at room temperature. The reaction mixture is acidified with 4 molar aqueous hydrochloric acid and extracted with ethyl acetate. The orgnaic phase is washed with saturated sodium chloride solution and concentrated by evaporation in a vacuum. 12 mg of the title compound is obtained.

$^1$H-NMR (300 MHz, CD$_3$OD): δ [ppm]=8.15 d (J=8 Hz, 1H, aryl); 8.10 d (J=2.1 Hz, 1H, aryl); 7.93 dd (J=8 Hz/2.1 Hz, 1H, aryl); 3.90 dd (J=9 Hz/6 Hz, 1H, CHN); 3.77 m (3H, CH$_2$N); 3.14 m (1H, CH$_2$N); 3.26 m (1H, CH$_2$N); 3.14 m (2H, CH$_2$N); 2.45 m (1H, CH$_2$); 2.14 m (2H, CH$_2$); 1.98 m (1H, CH$_2$); 1.89 m (2H, CH$_2$); 1.77 m (2H, CH$_2$); 1.60 s (6H, CH$_3$); 1.47 m (6H, CH$_2$).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Germany application No. 103 22 108.5, filed May 9, 2003, and U.S. Provisional Application Ser. No. 60/470,182, filed May 14, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I:

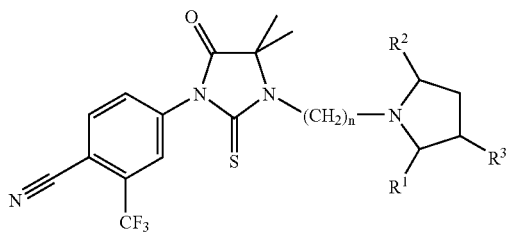

in which
n means an integer between 6 and 9,
R$^1$ and R$^2$, independently of one another, mean a hydrogen atom, an unbranched C$_1$–C$_4$-alkyl group, a branched C$_3$–C$_5$-alkyl group, an unbranched hydroxy-C$_1$–C$_4$-alkyl group, a branched hydroxy-C$_3$–C$_5$-alkyl group, an unbranched C$_1$–C$_4$-alkoxy-C$_1$–C$_4$-alkyl group, a branched C$_1$–C$_4$-alkoxy-C$_3$–C$_5$-alkyl group, an unbranched C$_1$–C$_4$-alkanoyloxy-C$_1$–C$_4$-alkyl group, a branched C$_1$–C$_4$-alkanoyloxy-C$_3$–C$_5$-alkyl group, a (pyrrolidin-1-yl)methyl group, a carboxy group, a C$_1$–C$_4$-alkoxycarbonyl group or an aminocarbonyl group, or
R$^1$ and R$^2$ together mean a 2-hydroxypropane-1,3-diyl bridge;
R$^3$ means a hydrogen atom or a hydroxy group,
or a pharmacologically acceptable salt thereof.

2. A compound of formula I according to claim 1, wherein R$^1$ represents a hydrogen atom, a hydroxymethyl group, an aminocarbonyl group or a methoxymethyl group; R$^2$ and R$^3$ in each case represent a hydrogen atom.

3. A compound of general formula I according to claim 1, wherein R$^1$ represents a hydrogen atom, or a methyl group; and R$^2$ and R$^3$ in each case represent a hydrogen atom.

4. A compound of general formula I according to claim 1, wherein R$^1$ and R$^2$ together represent a 2-hydroxypropane-1,3-diyl bridge; R$^3$ represents a hydrogen atom.

5. A compound according to claim 1, which is
4-[4,4-Dimethyl-5-oxo-3-[8-(pyrrolidin-1-yl)octyl]-2-thioxoimidazolidin-1-yl]-2-(trifluoromethyl)benzonitrile
4-[4,4-Dimethyl-5-oxo-3-[8-(pyrrolidin-1-yl)octyl]-2-thioxoimidazolidin-1-yl]-2-(trifluoromethyl)benzonitrile hydrochloride 4-[4,4-Dimethyl-5-oxo-3-[6-(pyrrolidin-1-yl)hexyl]-2-thioxoimidazolidin-1-yl]-2-(trifluoromethyl)benzonitrile 4-[4,4-Dimethyl-5-oxo-3-[7-(pyrrolidin-1-yl)heptyl]-2-thioxoimidazolidin-1-yl]-2-(trifluoromethyl)benzonitrile 4-[4,4-Dimethyl-5-oxo-3-[9-(pyrrolidin-1-yl)nonyl]-2-thioxoimidazolidin-1-yl]-2-(trifluoromethyl)benzonitrile 4-[3-[6-[(2R)-2-(Hydroxymethyl)pyrrolidin-1-yl]hexyl]-4,4-dimethyl-5-oxo-2-thioxoimidazolidin-1-yl]-2-(trifluoromethyl)benzonitrile 4-[3-[6-[(2S)-2-(Hydroxymethyl)pyrrolidin-1-yl]hexyl]-4,4-dimethyl-5-oxo-2-thioxoimidazolidin-1-yl]-2-(trifluoromethyl)benzonitrile 4-[3-[7-[(2R)-2-(Hydroxymethyl)pyrrolidin-1-yl]heptyl]-4,4-dimethyl-5-oxo-2-thioxoimidazolidin-1-yl]-2-(trifluoromethyl)benzonitrile 4-[3-[7-[(2S)-2-(Hydroxymethyl)pyrrolidin-1-yl]heptyl]-4,4-dimethyl-5-oxo-2-thioxoimidazolidin-1-yl]-2-(trifluoromethyl)benzonitrile 4-[3-[8-[(2R)-2-(Hydroxymethyl)pyrrolidin-1-yl]octyl]-4,4-dimethyl-5-oxo-2-thioxoimidazolidin-1-yl]-2-(trifluoromethyl)benzonitrile 4-[3-[8-[(2S)-2-(Hydroxymethyl)pyrrolidin-1-yl]octyl]-4,4-dimethyl-5-oxo-2-thioxoimidazolidin-1-yl]-2-(trifluoromethyl)benzonitrile 4-[3-[9-[(2R)-2-(Hydroxymethyl)pyrrolidin-1-yl]nonyl]-4,4-dimethyl-5-oxo-2-thioxoimidazolidin-1-yl]-2-(trifluoromethyl)benzonitrile 4-[3-[9-[(2S)-2-(Hydroxymethyl)pyrrolidin-1-yl]nonyl]-4,4-dimethyl-5-oxo-2-thioxoimidazolidin-1-yl]-2-(trifluoromethyl)benzonitrile 4-[3-[6-[(2R)-2-(Methoxymethyl)pyrrolidin-1-yl]hexyl]-4,4-dimethyl-5-oxo-2-thioxoimidazolidin-1-yl]-2-(trifluoromethyl)benzonitrile 4-[3-[6-[(2S)-2-(Methoxymethyl)pyrrolidin-1-yl]hexyl]-4,4-dimethyl-5-oxo-2-thioxoimidazolidin-1-yl]-2-(trifluoromethyl)benzonitrile 4-[3-[7-[(2R)-2-(Methoxymethyl)pyrrolidin-1-yl]heptyl]-4,4-dimethyl-5-oxo-2-thioxoimidazolidin-1-yl]-2-(trifluoromethyl)benzonitrile 4-[3-[7-[(2S)-2-(Methoxymethyl)pyrrolidin-1-yl]heptyl]-4,4-dimethyl-5-oxo-2-thioxoimidazolidin-1-yl]-2-(trifluoromethyl)benzonitrile 4-[3-[8-[(2R)-2-(Methoxymethyl)pyrrolidin-1-yl]octyl]-4,4-dimethyl-5-oxo-2-thioxoimidazolidin-1-yl]-2-(trifluoromethyl)benzonitrile 4-[3-[8-[(2S)-2-(Methoxymethyl)pyrrolidin-1-yl]octyl]-4,4-dimethyl-5-oxo-2-thioxoimidazolidin-1-yl]-2-(trifluoromethyl)benzonitrile 4-[3-[9-[(2R)-2-(Methoxymethyl)pyrrolidin-1-yl]nonyl]-4,4-dimethyl-5-oxo-2-thioxoimidazolidin-1-yl]-2-(trifluoromethyl)benzonitrile 4-[3-[9-[(2S)-2-(Methoxymethyl)pyrrolidin-1-yl]nonyl]-4,4-dimethyl-5-oxo-2-thioxoimidazolidin-1-yl]-2-(trifluoromethyl)benzonitrile 4-[3-[6-(3-Hydroxy-8-azabicyclo[3.2.1]oct-8-yl)hexyl]-4,4-dimethyl-5-oxo-2-thioxoimidazolidin-1-yl]-2-(trifluoromethyl)benzonitrile 4-[3-[7-(3-Hydroxy-8-azabicyclo[3.2.1]oct-8-yl)heptyl]-4,4-dimethyl-5-oxo-2-thioxoimidazolidin-1-yl]-2-(trifluoromethyl)benzonitrile 4-[3-[8-(3-Hydroxy-8-azabicyclo[3.2.1]oct-8-yl)octyl]-4,4-dimethyl-5-oxo-2-thioxoimidazolidin-1-yl]-2-(trifluoromethyl)benzonitrile 4-[3-[9-(3-Hydroxy-8-azabicyclo[3.2.1]oct-8-yl)nonyl]-4,4-dimethyl-5-oxo-2-thioxoimidazolidin-1-yl]-2-(trifluoromethyl)benzonitrile 4-[3-[6-[(R)-3-Hydroxypyrrolidin-1-yl]hexyl]-4,4-dimethyl-5-oxo-2-thioxoimidazolidin-1-yl]-2-(trifluoromethyl)benzonitrile 4-[3-[7-[(R)-3-Hydroxypyrrolidin-1-yl]heptyl]4,4-dimethyl-5-oxo-2-thioxoimidazolidin-1-yl]-2-(trifluoromethyl)benzonitrile 4-[3-[8-[(R)-3-Hydroxypyrrolidin-1-yl]octyl]-4,4-dimethyl-5-oxo-2-thioxoimidazolidin-1-yl]-2-(trifluoromethyl)benzonitrile 4-[3-[9-[(R)-3-Hydroxypyrrolidin-1-yl]nonyl]4,4-dimethyl-5-oxo-2-thioxoimidazolidin-1-yl]-2-(trifluoromethyl)benzonitrile 4-[3-[6-[(S)-3-Hydroxypyrrolidin-1-yl]hexyl]-4,4-dimethyl-5-oxo-2-thioxoimidazolidin-1-yl]-2-(trifluoromethyl)benzonitrile 4-[3-[7-[(S)-3-Hydroxypyrrolidin-1-yl]heptyl]-4,4-dimethyl-5-oxo-2-thioxoimidazolidin-1-yl]-2-(trifluoromethyl)benzonitrile 4-[3-[8-[(S)-3-Hydroxypyrrolidin-1-yl]octyl]-4,4-dimethyl-5-oxo-2-thioxoimidazolidin-1-yl]-2-(trifluoromethyl)benzonitrile 4-[3-[9-[(S)-3-Hydroxypyrrolidin-1-yl]nonyl]-4,4-dimethyl-5-oxo-2-thioxoimidazolidin-1-yl]-2-(trifluoromethyl)benzonitrile 4-[4,4-Dimethyl-3-[6-(2-methylpyrrolidin-1-yl)hexyl]-5-oxo-2-thioxoimidazolidin-1-yl]-2-(trifluoromethyl)benzonitrile 4-[4,4-Dimethyl-3-[7-(2-methylpyrrolidin-1-yl)heptyl]-5-oxo-2-thioxoimidazolidin-1-yl]-2-(trifluoromethyl)benzonitrile 4-[4,4-Dimethyl-3-[8-(2-methylpyrrolidin-1-yl)octyl]-5-oxo-2-thioxoimidazolidin-1-yl]-2-(trifluoromethyl)benzonitrile 4-[3-[8-[(2R,5S)-rel-2,5-Dimethylpyrrolidin-1-yl]octyl]-4,4-dimethyl-5-oxo-2-thioxoimidazolidin-1-yl]-2-(trifluoromethyl)benzonitrile 4-[3-[6-[(2S)-2-(1-Hydroxy-1-methylethyl)pyrrolidin-1-yl]hexyl]-4,4-dimethyl-5-oxo-2-thioxoimidazolidin-1-yl]-2-(trifluoromethyl)benzonitrile 4-[3-[7-[(2S)-2-(1-Hydroxy-1-methylethyl)pyrrolidin-1-yl]heptyl]-4,4-dimethyl-5-oxo-2-thioxoimidazolidin-1-yl]-2-(trifluoromethyl)benzonitrile 4-[3-[8-[(2S)-2-(1-Hydroxy-1-methylethyl)pyrrolidin-1-yl]octyl]-4,4-dimethyl-5-oxo-2-thioxoimidazolidin-1-yl]-2-(trifluoromethyl)benzonitrile 4-[3-[9-[(2S)-2-(1-Hydroxy-1-methylethyl)pyrrolidin-1-yl]nonyl]-4,4-dimethyl-5-oxo-2-thioxoimidazolidin-1-yl]-2-(trifluoromethyl)benzonitrile 4-[3-[6-[(2R)-2-(1-Hydroxy-1-methylethyl)pyrrolidin-1-yl]hexyl]-4,4-dimethyl-5-oxo-2-thioxoimidazolidin-1-yl]-2-(trifluoromethyl)benzonitrile 4-[3-[7-[(2R)-2-(1-Hydroxy-1-methylethyl)pyrrolidin-1-yl]heptyl]-4,4-dimethyl-5-oxo-2-thioxoimidazolidin-1-yl]-2-(trifluoromethyl)benzonitrile 4-[3-[8-[(2R)-2-(1-Hydroxy-1-methylethyl)pyrrolidin-1-yl]octyl]-4,4-dimethyl-5-oxo-2-thioxoimidazolidin-1-yl]-2-(trifluoromethyl)benzonitrile 4-[3-[6-[(2S)-2-(1-Hydroxy-1-ethylpropyl)pyrrolidin-1-yl]hexyl]-4,4-dimethyl-5-oxo-2-thioxoimidazolidin-1-yl]-2-(trifluoromethyl)benzonitrile 4-[3-[7-[(2S)-2-(1-Hydroxy-1-ethylpropyl)pyrrolidin-1-yl]heptyl]-4,4-dimethethyl-5-oxo-2-thioxoimidazolidin-1-yl]-2-(trifluoromethyl)benzonitrile 4-[3-[8-[(2S)-2-(1-Hydroxy-1-ethylpropyl)pyrrolidin-1-yl]octyl]-4,4-dimethyl-5-oxo-2-thioxoimidazolidin-1-yl]-2-(trifluoromethyl)benzonitrile (S)-1-[7-[3-[4-Cyano-3-(trifluoromethyl)phenyl]-5,5-dimethyl-4-oxo-2-thioxoimidazolidin-1-yl]heptyl]pyrrolidine-2-carboxylic acid methyl ester (S)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide (S)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide (S)-1-[8-[3-[4-Cyano-3-(trifluoromethyl)phenyl]-5,5-dimethyl-4-oxo-2-thioxoimidazolidin-1-yl]octyl]pyrrolidine-4-carboxamide (R)-1-[6-[3-[4-Cyano-3-(trifluoromethyl)phenyl]-5,5-dimethyl-4-oxo-2-thioxoimidazolidin-1-yl]hexyl]pyrrolidine-4-carboxamide (R)-1-[7-[3-[4-Cyano-3-(trifluoromethyl)phenyl]-5,5-dimethyl-4-oxo-2-thioxoimidazolidin-1-yl]heptyl]pyrrolidine-4-carboxamide (R)-1-[8-[3-[4-Cyano-3-(trifluoromethyl)phenyl]-5,5-dimethyl-4-oxo-2-thioxoimidazolidin-1-yl]octyl]pyrrolidine-4-carboxamide 4-[3-[6-[(2S)-4,4-Dimethyl-5-oxo-2-(pyrrolidin-1-ylmethyl)pyrrolidin-1-yl]hexyl]-2-thioxoimidazolidin-1-yl]-2-(trifluoromethyl)benzonitrile 4-[3-[7-[(2S)-4,4-Dimethyl-5-oxo-2-(pyrrolidin-1-ylmethyl)pyrrolidin-1-yl]heptyl]-2-thioxoimidazolidin-1-yl]-2-(trifluoromethyl)benzonitrile 4-[3-[8-[(2S)-4,4-Dimethyl-5-oxo-2-(pyrrolidin-1-ylmethyl)pyrrolidin-1-yl]octyl]-2-thioxoimidazolidin-1-yl]-2-(trifluoromethyl)benzonitrile or (S)-1-[7-[3-[4-Cyano-3-(trifluoromethyl)phenyl]-5,5-dimethyl-4-oxo-2-thioxoimidazolidin-1-yl]heptyl]pyrrolidine-2-carboxylic acid hydrochloride or pharmacologically accepted salts thereof.

6. A pharmaceutical composition comprising at least one compound of formula I or a pharmacologically acceptable salt thereof according to claim 1 and a pharmaceutically acceptable adjuvant and/or vehicle.

7. A method for the treatment of a disease of the human or animal body, which disease is prostate cancer, androgenetic alopecia, hirsutism, acne or benign prostate hyperplasia, comprising administering to a human or animal in need thereof an effective amount of a pharmaceutical composition according to claim 6.

8. A method according to claim 7, wherein the disease is an androgen-dependent proliferative disease.

9. A method according to claim 7, wherein the disease treated is a tumor disease.

10. A method according to claim 7, wherein the disease treated is prostate cancer.

11. A method according to claim 7, wherein the diseases is androgenetic alopecia, hirsutism or acne.

12. A method according to claim 7, wherein the diseases is benign prostate hyperplasia.

13. A process for the preparing an compound of formula I according to claim 1, comprising reacting a compound of formula II

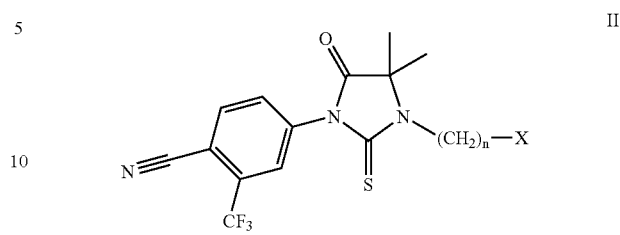

in which
n means an integer between 6 and 9,
X means a leaving group,
in the presence of an organic base with a compound of formula III

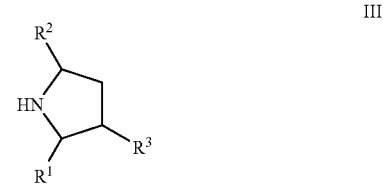

in which
$R^1$ and $R^2$, independently of one another, can mean a hydrogen atom, an unbranched $C_1$–$C_4$-alkyl group, a branched $C_3$–$C_5$-alkyl group, an unbranched hydroxy-$C_1$–$C_4$-alkyl group, a branched hydroxy-$C_3$–$C_5$-alkyl group, an unbranched $C_1$–$C_4$-alkoxy-$C_1$–$C_4$-alkyl group, a branched $C_1$–$C_4$-alkoxy-$C_3$–$C_5$-alkyl group, an unbranched $C_1$–$C_4$-alkanoyloxy-$C_1$–$C_4$-alkyl group, a branched $C_1$–$C_4$-alkanoyloxy-$C_3$–$C_5$-alkyl group, a (pyrrolidin-1-yl)methyl group, a carboxy group, a $C_1$–$C_4$-alkoxycarbonyl group or an aminocarbonyl group,
or
$R^1$ and $R^2$ together can mean a 2-hydroxypropane-1,3-diyl bridge; and
$R^3$ can means a hydrogen atom or a hydroxy group.

14. A pharmaceutical composition comprising at least one compound of formula I or pharmacologically acceptable salts thereof according to claim 5 and a pharmaceutically acceptable adjuvants and/or vehicle.

15. A method for treating prostate cancer comprising administering to a patient in need thereof an effective amount of a pharmaceutical composition according to claim 14.

16. A method for treating benign hyperplasia comprising administering to a patient in need thereof an effective amount of a pharmaceutical composition according to claim 14.

17. A method for treating androgenetic alopecia, hirsutism or acne comprising administering to a patient in need thereof an effective amount of a pharmaceutical composition according to claim 14.

18. A method for the treatment of a disease of the human or animal body, which disease is prostate cancer, androgenetic alopecia, hirsutism, acne or benign prostate hyperplasia, comprising administering to a human or an animal in need thereof an effective amount of a pharmaceutical composition according to claim 14.

* * * * *

UNITED STATES PATENT AND TRADEMARK OFFICE
CERTIFICATE OF CORRECTION

PATENT NO. : 7,138,421 B2  Page 1 of 1
APPLICATION NO. : 10/841825
DATED : November 21, 2006
INVENTOR(S) : Arwed Cleve It is certified that error appears in the above-identified patent and that said Letters Patent is hereby corrected as shown below:

On the Title page, Assignee: reads "Schring" should read -- Schering --
Column 61, line 41-42, reads "heptyl]4,4" should -- – heptl]-4,4 --
Column 62, line 14, reads "nonyl]4,4" should read -- nonyl]-4,4 --
Column 63, line 45, reads "accepted salts" should read -- acceptable salts --
Column 63, line 64, reads "the diseases" should read -- the disease --
Column 63, line 66, reads "the diseases" should read -- the disease --
Column 64, line 29, reads "can mean a" should read -- mean a --
Column 64, line 43, reads "can means a" should read -- means a --
Column 64, line 47, reads "acceptable adjuvants" should read -- acceptable adjuvant --
Column 64, line 63, reads "or an animal" should read -- or animal --

Signed and Sealed this

Tenth Day of July, 2007

JON W. DUDAS
*Director of the United States Patent and Trademark Office*